United States Patent [19]

Hopf et al.

[11] Patent Number: 4,886,620

[45] Date of Patent: Dec. 12, 1989

[54] SMECTIC LIQUID-CRYSTALLINE PHASES

[75] Inventors: Reinhard Hopf, Heringen, Fed. Rep. of Germany; Bernhard Scheuble, Yokohama, Japan; Andreas Wächtler, Griesheim, Fed. Rep. of Germany; Reinhard Hittich, Modautal, Fed. Rep. of Germany; Rudolf Eidenschink, Münster, Fed. Rep. of Germany; Thomas Geelhaar, Mainz, Fed. Rep. of Germany; Joachim Krause, Dieburg; Volker Reiffenrath, Darmstadt, all of Fed. Rep. of Germany

[73] Assignee: Merck Patent Gesellschaft mit Beschrankter Haftung, Darmstadt, Fed. Rep. of Germany

[21] Appl. No.: 51,120

[22] PCT Filed: Sep. 15, 1986

[86] PCT No.: PCT/EP86/00529

§ 371 Date: May 13, 1987

§ 102(e) Date: May 13, 1987

[87] PCT Pub. No.: WO87/01717

PCT Pub. Date: Mar. 26, 1987

[30] Foreign Application Priority Data

Sep. 18, 1985 [DE] Fed. Rep. of Germany ....... 3533333
Mar. 14, 1986 [DE] Fed. Rep. of Germany ....... 3608500

[51] Int. Cl.$^4$ .......................... G02F 1/13; C09K 19/34; C09K 19/30

[52] U.S. Cl. .......................... 252/299.61; 252/299.01; 252/299.6; 252/299.62; 252/299.63; 252/299.64; 252/299.65; 252/299.66; 252/299.67; 350/350 S

[58] Field of Search ........... 252/299.01, 299.6, 299.61, 252/299.62, 299.63, 299.65, 299.64, 299.67, 299.66; 350/350 S

[56] References Cited

U.S. PATENT DOCUMENTS 4,235,736 11/1980 Beguin et al. .............. 252/299.65

(List continued on next page.)

FOREIGN PATENT DOCUMENTS

| 84194 | 7/1983 | European Pat. Off. ........ 252/299.61 |
| 156726 | 10/1985 | European Pat. Off. ........ 252/299.64 |
| 178647 | 4/1986 | European Pat. Off. ........ 252/299.01 |
| 3525015 | 1/1986 | Fed. Rep. of Germany ........ 252/299.66 |
| 3510434 | 9/1986 | Fed. Rep. of Germany ........ 252/299.63 |
| 3515374 | 11/1986 | Fed. Rep. of Germany ........ 252/299.61 |
| 3518734 | 11/1986 | Fed. Rep. of Germany ........ 252/299.61 |
| 3706766 | 9/1987 | Fed. Rep. of Germany ........ 252/299.60 |
| 61-229842 | 10/1986 | Japan .............................. 252/299.01 |
| 61-243037 | 10/1986 | Japan .............................. 252/299.01 |
| 61-246168 | 11/1986 | Japan .............................. 252/299.61 |
| 8705013 | 8/1987 | World Int. Prop. O. ...... 252/299.63 |

OTHER PUBLICATIONS

Dubois, J. C., et al., Mol. Cryst. Liq Cryst., vol. 42, No. 1–3, pp. 139–152 (1977).

Primary Examiner—Teddy S. Gron
Attorney, Agent, or Firm—Millen, White & Zelano

[57] ABSTRACT

The invention relates to the use of compounds of the formula I $$R^1-Q^1-A-(A^2)_q-R^2 \qquad I$$

wherein

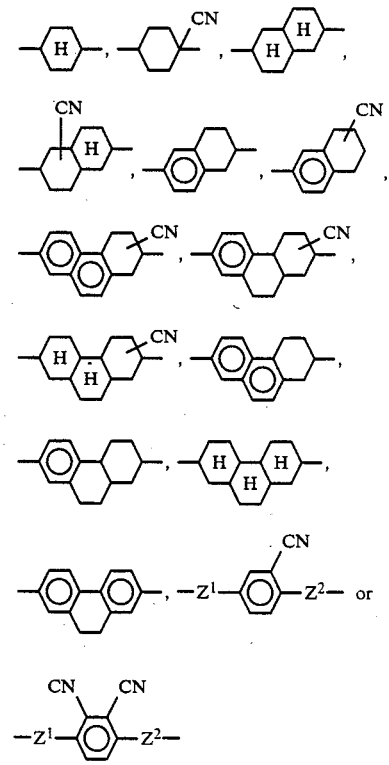

and $R^1$, $R^2$, $Q^1$, $Q^2$ and q have the meaning specified in claim 1, as components of smectic liquid-crystalline phases, and also smectic liquid-crystalline phases, in particular chiral tilted smectic phases containing compounds of formula I.

9 Claims, No Drawings

U.S. PATENT DOCUMENTS

| | | | |
|---|---|---|---|
| 4,279,770 | 7/1981 | Inukai et al. | 252/299.63 |
| 4,402,855 | 9/1983 | Zann et al. | 252/299.65 |
| 4,434,073 | 2/1984 | Sucron et al. | 252/299.62 |
| 4,474,740 | 10/1984 | Eidenschink et al. | 252/299.63 |
| 4,510,069 | 4/1985 | Eidenschink et al. | 252/299.63 |
| 4,600,528 | 7/1986 | Eidenschink et al. | 252/299.62 |
| 4,622,163 | 11/1986 | Huynh-Ba et al. | 252/299.61 |
| 4,629,581 | 12/1986 | Boller et al. | 252/299.63 |
| 4,637,897 | 1/1987 | Kelly | 252/299.63 |
| 4,659,502 | 4/1987 | Fearon et al. | 252/299.63 |
| 4,693,841 | 9/1987 | Hittich et al. | 252/299.62 |
| 4,707,295 | 11/1987 | Pohl et al. | 252/299.63 |
| 4,723,005 | 2/1988 | Huynh-Ba et al. | 252/299.63 |
| 4,726,911 | 2/1988 | Krause et al. | 252/299.61 |
| 4,737,311 | 4/1988 | Scheuble et al. | 252/299.61 |
| 4,737,313 | 4/1988 | Saito et al. | 252/299.65 |
| 4,752,414 | 6/1988 | Eidenschink | 252/299.61 |
| 4,776,973 | 10/1988 | Bofinger et al. | 252/299.61 |
| 4,780,241 | 10/1986 | Furukawa et al. | 252/299.63 |
| 4,812,258 | 3/1989 | Krause et al. | 252/299.61 |
| 4,818,428 | 4/1989 | Scheuble et al. | 252/299.61 |
| 4,820,839 | 4/1989 | Krause et al. | 252/299.61 |

SMECTIC LIQUID-CRYSTALLINE PHASES

The invention relates to the use of compounds of the formula I $$R^1-Q^1-A-(Q^2)_q-R^2 \qquad I$$

wherein $R^1$ and $R^2$ each denote independently of each other an alkyl group or a polyfluoroalkyl group containing 1 to 15 C atoms in each case, wherein one or more $CH_2$ groups or $CF_2$ groups may also be replaced by a grouping selected from the group comprising —O—, —S—, —CO—, —CHhalogen—, —CHCN—, —O—CO—, —O—COO—, —CO—O— and —CH=CH— or else by a combination of two suitable groupings, two hetero atoms not being directly linked to each other, and one of the radicals $R^1$ and $R^2$ also being halogen, A denotes

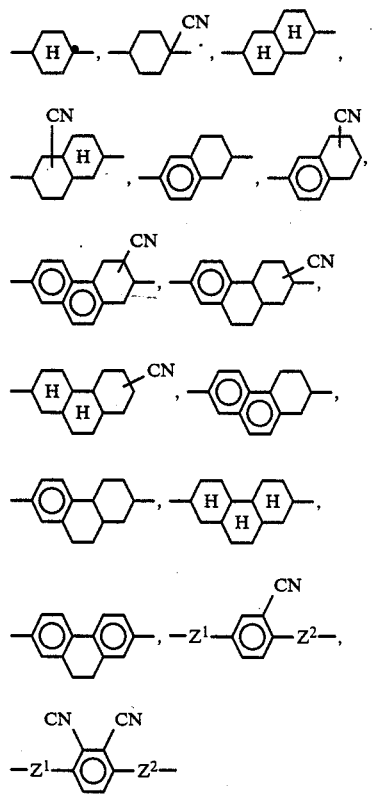

or one of these groups, wherein one or more $CH_2$ groups are replaced by O and/or S or aliphatic and/or aromatic CH groups are replaced by N, q denotes 0 or 1, $Q^1$ and $Q^2$ each denote independently of each other —$(A°-Z°)_p$—, where A° denotes unsubstituted 1,4-cyclohexylene or 1,4-cyclohexylene substituted singly or multiply by halogen atoms, $CH_3$ and/or nitrile groups, wherein one or two nonadjacent $CH_2$ groups may also be replaced by —O— and/or —S— and/or a

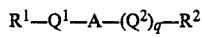

grouping may be replaced by

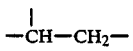 (Cy), or unsubstituted 1,4-phenylene or 1,4-phenylene substituted singly or multiply by halogen atoms, $CH_3$— and/or nitrile groups, wherein one or more CH groups may also be replaced by N (Ph), one of the radicals A° may also stand for 2,6-naphthylene (Na) or tetrahydro-2,6-naphthylene (4H-Na), optionally substituted by halogen or CN, Z°, $Z^1$ and $Z^2$ each denote independently of each other —CO—O—, —O—CO—, —$CH_2O$—, —$OCH_2$—, —$CH_2CH_2$—, —CHCN—$CH_2$—, —$CH_2$—CHCN— or a single bond, and P denotes 1, 2 or 3, or if A=tetra- or octahydrophenanthrene, also 0, and if A=

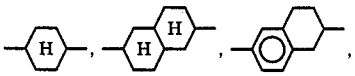

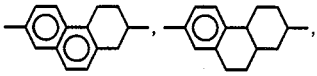

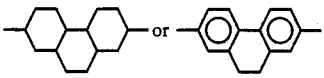

at least one group Z° denotes —$CHCNCH_2$ or —$CH_2CHCN$— and/or in at least one of the groups $R^1$ and $R^2$ at least one $CH_2$ group or $CF_2$ group is replaced by —CHCN—, as components of smectic liquid-crystalline phases, and also smectic liquid-crystalline phases, in particular chiral tilted smectic phases containing compounds of the formula I.

Chiral tilted smectic liquid-crystalline phases with ferroelectric properties can be prepared by adding a suitable chiral dopant to basic mixtures having one or more tilted smectic phases (L. A. Beresnev et al., Mol. Cryst. Liq. Cryst. 89, 327 (1982); H. R. Brand et al., J. Physique 44, (lett.), L-771 (1983)). Such phases can be used as dielectrics for fast-switching displays which are based on the principle of SSFLC technology described by Clark and Lagerwall (N. A. Clark and S. T. Lagerwall, Appl. Phys. Lett. 36, 899 (1980); U.S. Pat. No. 4,367,924) based on the ferroelectric properties of the chiral tilted phase. In said phase the long molecules are arranged in layers, the molecules having an angle of tilt to a line perpendicular to the layer. On proceeding from layer to layer, the direction of tilt changes by a small angle with respect to an axis situated perpendicular to the layers so that a helical structure is formed. In displays which are based on the principle of SSFLC technology the smectic layers are arranged perpendicularly to the plates of the cell. The helical arrangement of the tilt directions of the molecules is suppressed by a very small spacing of the plates (approx. 1-2 μm). As a result the longitudinal axes of the molecules are forced to arrange themselves in a plane parallel to the plates of the cell, as a result of which two distinct tilt orientations are produced. By applying a suitable alternating electric field it is possible to switch back and forth between these two states in the liquid-crystalline phase which exhibits a spontaneous polarization. Said switching process is substantially faster than in the case of conventional twisted cells (TN LCDs) which are based on nematic liquid crystals.

A considerable disadvantage for many applications of the materials at present available with chiral tilted smectic phases (such as, for example, Sc*) is that the dielectric anisotropy has values greater than zero or, if negative, values only slightly different from zero. Negative values of the dielectric anisotropy are necessary if the necessary planar orientation is produced by superimposing an AC holding field with low amplitude on the drive field (J. M. Geary, SID Conference, Orlando/Fla., Apr./May 1985, Paper 8.3). The use of materials with strongly negative dielectric anisotropy generally leads to a strong decrease in the spontaneous polarization and/or to unfavourable values for pitch and/or tilt. In addition, the temperature range of the ferroelectric phases is generally restricted in an unfavourable manner.

It has now been found that the use of compounds of formula I as components of chiral tilted smectic mixtures may substantially reduce the disadvantages mentioned. The compounds of formula I are therefore excellently suitable as components of chiral tilted smectic liquid-crystalline phases. In particular, chemically especially stable chiral tilted smectic liquid-crystalline phases with favourable ferroelectric phase ranges, in particular with broad Sc* phase ranges, negative dielectric anisotropy, favourable pitch height and values of spontaneous polarization which are high for such phases can be prepared with their aid. P is the spontaneous polarization in $nC/cm^2$.

The compounds of formula I have a wide field of application. Depending on the choice of substituents, said compounds may serve as basic materials of which liquid-crystalline smectic phases are predominantly composed; compounds of formula I can, however, also have added to them liquid-crystalline basic materials from other compound classes, in order, for example, to vary the dielectric and/or optical anisotropy and/or the viscosity and/or the spontaneous polarization and/or the phase range and/or the tilt angle and/or the pitch of such a dielectric. However, optically active compounds of formula I can also be used as dopants for basic mixtures, the basic mixtures consisting of materials from other compound classes or entirely or partly of achiral (racemate or components of formula I without a centre of asymmetry) or other chiral compounds of formula I.

The subject of the invention is thus the use of the compounds of formula I as components of (chiral tilted) smectic liquid-crystalline phases. The subject of the invention is further formed by smectic liquid-crystalline phases, in particular chiral tilted smectic phases, with a content of at least one compound of formula I and also liquid-crystalline display elements, in particular electro-optical display elements which contain such phases.

The compounds of formula I may have straight-chain or branched wing groups $R^1$ and/or $R^2$. The compounds having branched wing groups may be used in the form of the racemate or as optically active compounds. Achiral basic mixtures consisting of compounds of formula I and optionally further achiral components may be doped with chiral compounds of formula I or also with other chiral compounds in order to obtain chiral tilted smectic phases.

The compounds of formula I comprise in particular compounds of the partial formulae Ia to In:

| | |
|---|---|
| $R^1—Q^1—A—R^2$ | Ia |
| $R^1—Q^1—A—Ph—R^2$ | Ib |
| $R^1—Q^1—A—Cy—R^2$ | Ic |
| $R^1Q^1—A—Cy—Ph—R^2$ | Id |
| $R^1—Q^1—A—Ph—Cy—R^2$ | Ie |
| $R^1—Q^1—A—Ph—Ph—R^2$ | If |
| $R^1—Q^1—A—Cy—Cy—R^2$ | Ig |
| $R^1—Q^1—A—Ph—Ph—Cy—R^2$ | Ih |
| $R^1—Q^1—A—Cy—Ph—Ph—R^2$ | Ii |
| $R^1—Q^1—A—Na—R^2$ | Ij |
| $R^1—Q^1—A—4H—Na—R^2$ | Ik |
| $R^1—Q^1—A—Z^o—A^o—R^2$ | Il |
| $R^1—Q^1—A—Z^o—A^o—A^o—R^2$ | Im |
| $R^1—Q^1—A—A^o—Z^o—A^o—R^2$ | In |

Of these, those of partial formula Ia, Ib, Ic and Il are preferred in particular.

The preferred compounds of partial formula Ia comprise those of partial formula Iaa to Ian:

| | |
|---|---|
| $R^1—Ph—A—R^2$ | Iaa |
| $R^1—Cy—A—R^2$ | Iab |
| $R^1—Cy—Ph—A—R^2$ | Iac |
| $R^1—Ph—Cy—A—R^2$ | Iad |
| $R^1—Ph—Ph—A—R^2$ | Iae |
| $R^1—Cy—Cy—A—R^2$ | Iaf |
| $R^1—Ph—Ph—Cy—A—R^2$ | Iag |
| $R^1—Cy—Ph—Ph—A—R^2$ | Iah |
| $R^1—Na—A—R^2$ | Iai |
| $R^1—4H—Na—A—R^2$ | Iaj |
| $R^1—A^o—A^o—Z^o—A—R^2$ | Iak |
| $R^1—A^o—Z^o—A^o—A—R^2$ | Ial |
| $R^1—A^o—Z^o—A—R^2$ | Iam |
| $R^1—A^o—A—Z^o—A^o—R^2$ | Ian |

A° and Z° may be identical or different, if p denotes 2 or 3.

Particularly preferred are compounds of the formulae Iah, Ial, Iam and Ian, wherein $R^1$ denotes alkyl, alkoxy, alkanoyloxy, alkoxycarbonyl or alkoxycarbonyloxy, A° denotes trans-1,4-cyclohexylene or 1,4-phenylene (optionally laterally substituted by a fluorine atom) and Z° denotes —CO—O—, —O—CO— or —$CH_2CH_2$—, or if A is trans-1,4-cyclohexylene also —$CH_2$—CHCN— or —CHCN—$CH_2$—. $R^2$ is preferably alkyl or alkyl in which a $CH_2$ group has been replaced by —CHCN—.

Of these, those of the partial formula Iaa, Iac, Iad, Iae, Iaf, Iah, Iak, Ial, Iam and Ian are preferred. Particularly preferred are those of the partial formulae Iaa, Iac, Iae, Iah, Iak and Ial, in particular Iae, in which $R^1$ and $R^2$ denote branched or straight-chain alkyl groups or alkyloxy groups containing 3 to 12 C atoms and Iaa, in which $R^1$ denotes branched or straight-chain alkoxy, alkanoyloxy, alkoxycarbonyl or alkoxycarbonyloxy.

The preferred compounds of the partial formula Iak comprise those of the partial formulae Iaka to Iakc:

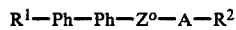    Iak

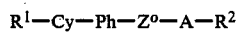    Iakb

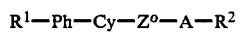    Iakc in which $Z^o$ preferably denotes —CO—O—, —O—CO—, —CH$_2$CH$_2$—, —CH$_2$O— or —OCH$_2$, and preferred in particular —CO—O—, —O—CO— or —CH$_2$CH$_2$—or if —O—CO— or —CH$_2$CH$_2$— or

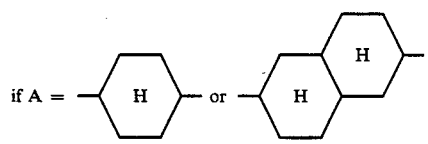

also —CHCN—CH$_2$— or —CH$_2$—CHCN—.

In compounds of the formula I, wherein A denotes

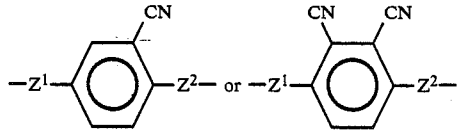

q is preferably 1 and the other rings $A^o$ are preferably not laterally substituted. Compounds of this type contain preferably one, particularly preferably, two trans-1,4-cyclohexylene groups.

The preferred compounds of the partial formula Ial comprise those of partial formulae Iala to Ialc:

    IaLa

    IaLb

    IaLc wherein $Z^o$ preferably denotes —CO—O—, —O—CO—, —CH$_2$CH$_2$—, —CH$_2$O— or —OCH$_2$, preferred in particular —CO—O—, —O—CO— or —CH$_2$CH$_2$—, or if

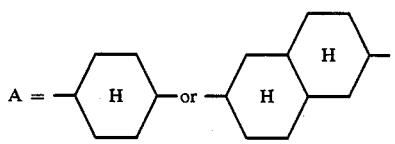

also —CHCN—CH$_2$— or —CH$_2$—CHCN—.

The preferred compounds of partial formula Ib comprise those of the partial formulae Iba and Ibb:

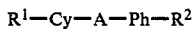    Iba

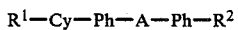    Ibb

Of these, those of the partial formula Iba are preferred in particular.

The preferred compounds of the partial formula Ic comprise those of the partial formulae Ica to Ice:

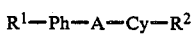    Ica

    Icb

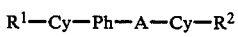    Icc

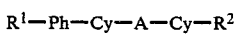    Icd

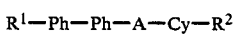    Ice

Of these, those of the partial formula Icb are preferred in particular.

Particularly preferred $Q^1$ and $Q^2$ groups are those of the formulae 1 to 41:

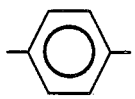    1

    2

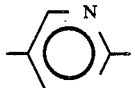    3

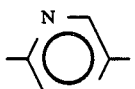    4

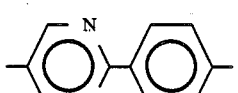    5

    6

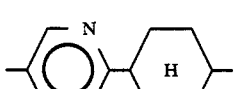    7

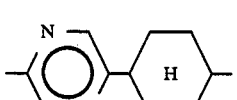    8

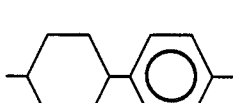    9

-continued
| | |
|---|---|
| 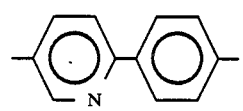 | |
| 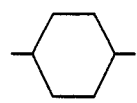 | |
| 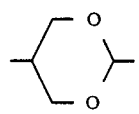 | |
| 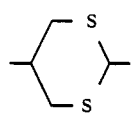 | |
| 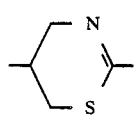 | |
| 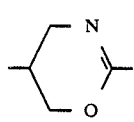 | |
| 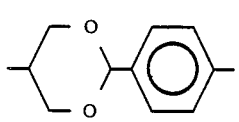 | |
| 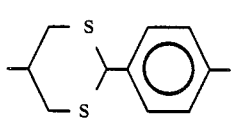 | |
| 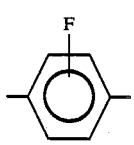 | |
| 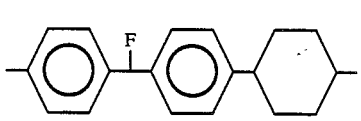 | |
| 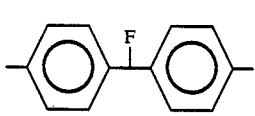 | |
| 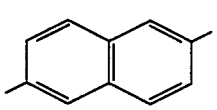 | |
| 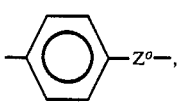 | |
-continued
| | |
|---|---|
| 9a 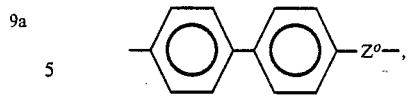 | 22 |
| 10 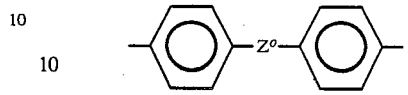 | 23 |
| 11 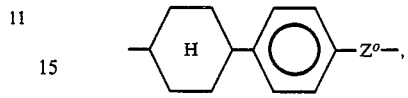 | 24 |
| 12 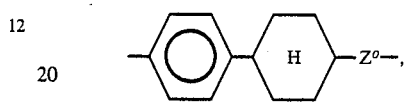 | 25 |
| 13 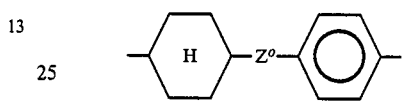 | 26 |
| 14 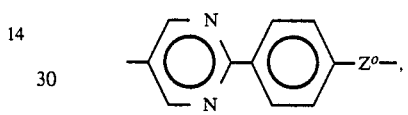 | 27 |
| 15 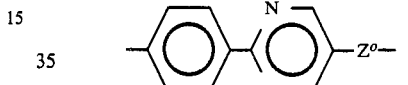 | 28 |
| 16 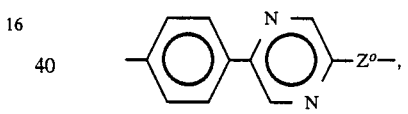 | 29 |
| 17 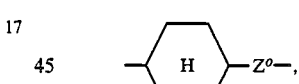 | 30 |
| 18 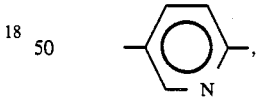 | 31 |
| 19 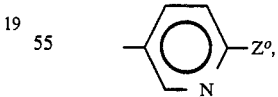 | 32 |
| 20 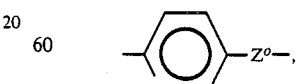 | 33 |
| 21 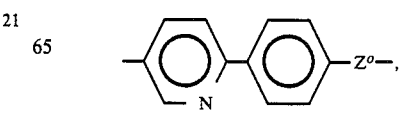 | 34 |

-continued

35

$$-\underset{F}{\phantom{a}}\!\!\!\!\bigcirc\!\!\!\!-Z^{o}-,$$

36

$$-\bigcirc-COO-\bigcirc-,$$

37

$$-\bigcirc-COO-\bigcirc-,$$

38

$$-\bigcirc-OCO-\bigcirc-,$$

39

$$-CH_2CH_2-\bigcirc-,$$

40

$$-\underset{F}{\phantom{a}}\!\!\!\!\bigcirc\!\!\!\!-\bigcirc-$$

41

$$-\underset{CN}{\phantom{a}}\!\!\!\!\bigcirc\!\!\!\!-\bigcirc-$$

and also combinations thereof which do not exceed three rings. The mirror images of the unsymmetrical above formulae are also suitable. In the above formula, the formula $$\underset{F}{\phantom{a}}\!\!\!\!\bigg|$$

represents 2- or 2′-fluoro biphenylene substitution.

Preferred are the groups of formulae 1, 2,·3, 5, 6, 7, 9, 10, 18, 19, 21, 22, 23, 24, 25, 26, 27, 29, 30, 34 and 36 to 41.

Preferably one of the radicals $Q^1$ and $Q^2$ is Cy, Cy—$Z^o$ or a single bond; preferred in particular is a single bond and for the other radical $Q^1$ or $Q^2$ a group of the formula 2, 5, 6, 7, 8, 9, 18 or 19.

A is preferably a group of the formula (A)

(A)

$$\bigg\langle\!\!\!\!\bigcirc\!\!\!\!\underset{CN}{\phantom{a}}$$

or the mirror image thereof in the specified configuration with axial nitrile group and transposition of the substituents $Q^1$ and $Q^2$ or trans-1,4-cyclohexylene.

Compounds of the formula I are furthermore preferred wherein A denotes trans-1,4-cyclohexylene, and in one of the groups $R^1$ and $R^2$, a $CH_2$ or $CF_2$ group is replaced by —CHCN— and/or a $Z^o$ group denotes —CHCNCH$_2$— or —CH$_2$CHCN—.

In the compounds of the formulae above and below $R^1$ and $R^2$ preferably denote R—, R—O—, R—O—CO—, R—O—COO— or R—CO—O—. R is preferably a straight-chain alkyl group with preferably 5 to 12 C atoms, wherein one or two non-terminal CH$_2$ groups may be replaced by —O—, —O—CO—, —CHCH$_3$, —CHCN—, —CHhalogen, —CHCH$_3$—O— and/or —CH=CH—. R denotes, for example, preferably pentyl, hexyl, heptyl, octyl, nonyl, decyl, undecyl or dodecyl, also methyl, ethyl, propyl, butyl, 2-, 3- or 4-oxapentyl, 2-, 3-, 4- or 5-oxahexyl, 2-, 3-, 4-, 5-or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6-or 4,6-dioxaheptyl, 1,4-dioxaoctyl, 1,4,7-trioxaoctyl, 1,4-dioxanonyl or 1,4-dioxadecyl.

Compounds of formula I and also of the partial formulae above and below with branched wing groups $R^1$ or $R^2$ may occasionally be of importance because of a better solubility in the usual liquid-crystalline basic materials, in particular, however, as chiral dopants for chiral tilted smectic phases if they are optically active. Such compounds are suitable, however, also as components of nematic liquid-crystalline phases, in particular to prevent reverse twist. Branched groups of this type as a rule contain one or two chain branches. Preferably the asymmetric carbon atom is linked to two differently substituted C atoms, an H atom and a substituent chosen from the group consisting of halogen (in particular F, Cl or Br), alkyl or alkoxy containing in each case 1 to 5 C atoms and CN. The optically active organic radical $R^1$ or $R^2$ has preferably the formula $$-X-Q-\overset{*}{\underset{Y}{C}H}-R$$

wherein

X denotes —CO—O, —O—CO—, —O—CO—O—, —CO—, —O—, —S—, —CH=CH—, —CH=CH—COO— or a single bond, Q denotes alkylene containing 1 to 5 C atoms, wherein a $CH_2$ group not linked to X may also be replaced by —O—, —CO—, —O—CO—, —CO—O— or —CH=CH—, or a single bond, Y denotes CN, halogen, methyl or methoxy, and R denotes an alkyl group differing from Y and containing 1 to 18 C atoms wherein one or two nonadjacent CH$_2$ groups may also be replaced by —O—, —CO—, —O—CO—, —CO—O— and/or —CH=CH—.

X is preferably —CO—O—, —O—CO—, —CH=CH—COO— (trans) or a single bond. Especially preferred are —CO—O— and —O—CO—.

Q is preferably —CH$_2$—, —CH$_2$CH$_2$— or a single bond, preferred in particular is a single bond.

Y is preferably CH$_3$, —CN or Cl, preferred in particular is —CN.

R is preferably straight-chain alkyl containing 1 to 10, in particular containing 1 to 7, C atoms.

Preferred branched radicals are isopropyl, 2-butyl (=1-methylpropyl), isobutyl (=2-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl.

Compounds of the formula I, wherein one of the radicals R$^1$ and R$^2$ has the formula —X—Q—*CHC-N—R (with the preferred meanings specified above) can be prepared, for example, as described by D. A. Evans and J. M. Takacs, Tetrahedron Lett. 21, 4233 (1980).

Polyfluoroalkylene groups, wherein one or more CF$_2$ groups may also be replaced by a grouping selected from the group comprising —O—, —S—, —CO—, —CHhalogen—, —CHCN—, —O—CO—, —O—COO—, —CO—O— and —CH=CH—, or else by a combination of two suitable groupings, two hetero atoms not being directly linked to each other, preferably denote perfluoroalkyl groups containing 1 to 15 C atoms, wherein 1 to 3 CF$_2$ groups may also be replaced by a grouping selected from the group comprising —O—, —CHhalogen— (in particular —CHF—), —O—CO—, —CO—O— and —O—COO—, or else by a combination of two suitable groupings, two hetero atoms not being directly linked with each other.

Especially preferred groups are those of the formulae R$_F$, R$_F$CH$_2$, R$_F$CH$_2$CH$_2$, R$_F$CH$_2$O and R$_F$COO.

R$_F$ is preferably a straight-chain perfluoroalkyl group containing preferably 2 to 12 C atoms, wherein one or more fluorine atoms (preferably 1 or 2 fluorine atoms, preferably in the ω- or (ω-1) position) may be replaced by H.

Preferred compounds of the formula I, wherein at least one of the radicals R$^1$ and R$^2$ is a polyfluoroalkyl group, result in phases according to the invention with low optical anisotropy and pronounced S$_A$ phase at elevated temperatures.

Of the compounds of formula I and also of the partial formulae above and below those are preferred in which at least one of the radicals contained therein has one of the specified preferred meanings. Particularly preferred smaller groups of compounds are those of formulae I1 to I18:

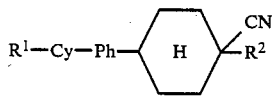
I1

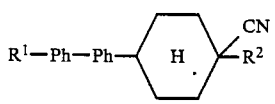
I2

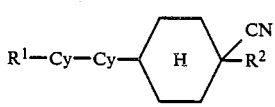
I3

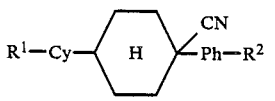
I4

-continued

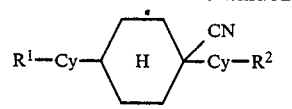
I5

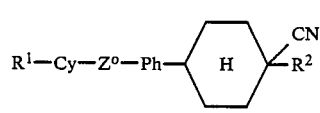
I6

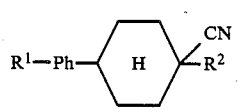
I7

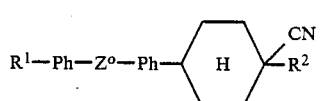
I8

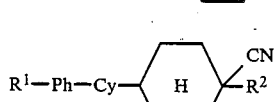
I9

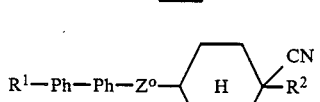
I10

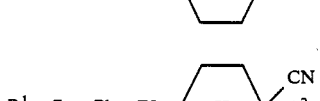
I11

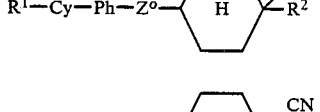
I12

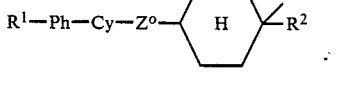
I13

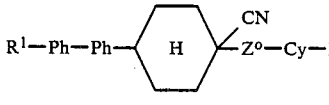
I14

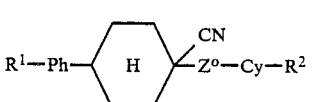
I15

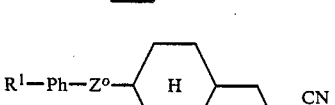
I16

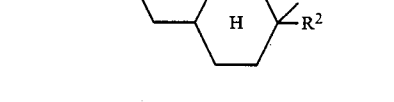
I17

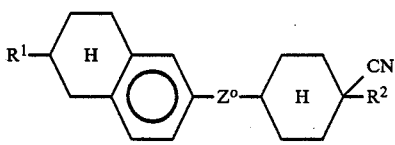 I18

A further specially preferred smaller group of compounds are those of formulae I19 to I22:

$R^1—A^o—Cy—(CH_2)_r—CHCN—C_sH_{2s+1}$  I19

$R^1—A^o—A^o—Cy—(CH_2)_r—CHCN—C_sH_{2s+1}$  I20

$R^1—A^o—A^o—CHCN—CH_2—Cy—R^2$  I21

$R^1—A^o—A^o—CH_2—CHCN—Cy—R^2$  I22 where r denotes 0, 1, 2 or 3 and (r+s) is 1 to 14.

A further specially preferred smaller group of compounds are those of the formulae I23 to I26:

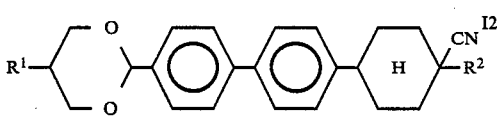 I23

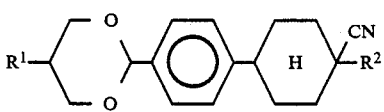 I24

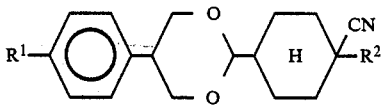 I24a

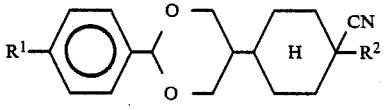 I24b

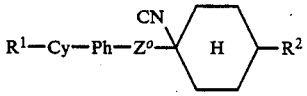 I25

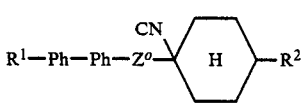 I26

In the especially preferred compounds of the formulae I2, I10 and I26, —Ph—Ph— preferably denotes a group of the formula 2, 5, 9a or 19 (it being possible for fluorine to be in the 2-,3-,2'- or 3'-position). Especially preferred are 2 and 40.

Compounds of formula I which exhibit no $S_c$ phases are also suitable as components of the smectic phases according to the invention.

Particularly preferred compounds of formula I are specified in the following:

4-(4-cyano-4-butylcyclohexyl)-4'-heptylbiphenyl, m.p. 56°, c.p. 122°

4-(4-cyano-4-butylcyclohexyl)-4'-octylbiphenyl, m.p. 42°, c.p. 118°

4-(4-cyano-4-butylcyclohexyl)-4'-nonylbiphenyl 4-(4-cyano-4-butylcyclohexyl)-4'-butoxybiphenyl 4-(4-cyano-4-butylcyclohexyl)-4'-pentoxybiphenyl 4-(4-cyano-4-butylcyclohexyl)-4'-hexoxybiphenyl 4-(4-cyano-4-butylcyclohexyl)-4'-heptoxybiphenyl, m.p. 93°, c.p. 156°

4-(4-cyano-4-butylcyclohexyl)-4'-octoxybiphenyl, m.p. 80°, c.p. 154°

4-(4-cyano-4-butylcyclohexyl)-4'-nonoxybiphenyl, m.p. 89°, c.p. 150°

4-(4-cyano-4-pentylcyclohexyl)-4'-ethylbiphenyl 4-(4-cyano-4-pentylcyclohexyl)-4'-propylbiphenyl 4-(4-cyano-4-pentylcyclohexyl)-4'-butylbiphenyl, m.p. 75°, c.p. 128°

4-(4-cyano-4-pentylcyclohexyl)-4'-pentylbiphenyl 4-(4-cyano-4-pentylcyclohexyl)-4'-hexylbiphenyl 4-(4-cyano-4-pentylcyclohexyl)-4'-heptylbiphenyl, m.p. 54°, c.p. 127°

4-(4-cyano-4-pentylcyclohexyl)-4'-octylbiphenyl, m.p. 43°, c.p. 115°

4-(4-cyano-4-pentylcyclohexyl)-4'-nonylbiphenyl 4-(4-cyano-4-pentylcyclohexyl)-4'-butoxybiphenyl 4-(4-cyano-4-pentylcyclohexyl)-4'-pentoxybiphenyl 4-(4-cyano-4-pentylcyclohexyl)-4'-hexoxybiphenyl 4-(4-cyano-4-pentylcyclohexyl)-4'-heptoxybiphenyl, m.p. 91°, c.p. 161°

4-(4-cyano-4-pentylcyclohexyl)-4'-octoxybiphenyl, m.p. 93°, c.p. 160°

4-(4-cyano-4-pentylcyclohexyl)-4'-nonoxybiphenyl, m.p. 83°, c.p. 156°

4-(4-cyano-4-hexylcyclohexyl)-4'-ethylbiphenyl

4-[4-cyano-4-(2-methylbutylcyclohexyl)]-4'-ethylbiphenyl

4-[4-cyano-4-(2-methylbutylcyclohexyl)]-4'-propylbiphenyl

4-[4-cyano-4-(2-methylbutylcyclohexyl)]-4'-butylbiphenyl

4-[4-cyano-4-(2-methylbutylcyclohexyl)]-4'-pentylbiphenyl

4-[4-cyano-4-(2-methylbutylcyclohexyl)]-4'-hexylbiphenyl

4-[4-cyano-4-(2-methylbutylcyclohexyl)]-4'-heptylbiphenyl

4-[4-cyano-4-(2-methylbutylcyclohexyl)]-4'-octylbiphenyl

4-[4-cyano-4-(2-methylbutylcyclohexyl)]-4'-nonylbiphenyl

4-[4-cyano-4-(2-methylbutylcyclohexyl)]-4'-butoxybiphenyl

4-[4-cyano-4-(2-methylbutylcyclohexyl)]-4'-pentoxybiphenyl

4-[4-cyano-4-(2-methylbutylcyclohexyl)]-4'-hexoxybiphenyl

4-[4-cyano-4-(2-methylbutylcyclohexyl)]-4'-heptoxybiphenyl m.p. 66°, c.p. 131.4°, 131.0° Ch/Bp 4-[4-cyano-4-(2-methylbutylcyclohexyl)]-4'-octoxybiphenyl 4-[4-cyano-4-(2-methylbutylcyclohexyl)]-4'-nonoxybiphenyl 4-(4-cyano-4-hexylcyclohexyl)-4'-propylbiphenyl 4-(4-cyano-4-hexylcyclohexyl)-4'-butylbiphenyl 4-(4-cyano-4-hexylcyclohexyl)-4'-pentylbiphenyl 4-(4-cyano-4-hexylcyclohexyl)-4'-hexylbiphenyl 4-(4-cyano-4-hexylcyclohexyl)-4'-heptylbiphenyl, m.p. 66°, c.p. 125°

4-(4-cyano-4-hexylcyclohexyl)-4'-octylbiphenyl 4-(4-cyano-4-hexylcyclohexyl)-4'-nonylbiphenyl 4-(4-cyano-4-hexylcyclohexyl)-4'-butoxybiphenyl 4-(4-cyano-4-hexylcyclohexyl)-4'-pentoxybiphenyl
4-(4-cyano-4-hexylcyclohexyl)-4'-hexoxybiphenyl
4-(4-cyano-4-hexylcyclohexyl)-4'-heptoxybiphenyl, m.p. 88°, c.p. 156°
4-(4-cyano-4-hexylcyclohexyl)-4'-octoxybiphenyl, m.p. 90°, c.p. 155°
4-(4-cyano-4-hexylcyclohexyl)-4'-nonoxybiphenyl, m.p. 87°, c.p. 152°
4-(4-cyano-4-heptylcyclohexyl)-4'-ethylbiphenyl
4-(4-cyano-4-heptylcyclohexyl)-4'-propylbiphenyl
4-(4-cyano-4-heptylcyclohexyl)-4'-butylbiphenyl
4-(4-cyano-4-heptylcyclohexyl)-4'-pentylbiphenyl
4-(4-cyano-4-heptylcyclohexyl)-4'-hexylbiphenyl
4-(4-cyano-4-heptylcyclohexyl)-4'-heptylbiphenyl, m.p. 61°, c.p. 124°
4-(4-cyano-4-heptylcyclohexyl)-4'-octylbiphenyl, m.p. 64°, c.p. 125°
4-(4-cyano-4-heptylcyclohexyl)-4'-nonylbiphenyl
4-(4-cyano-4-heptylcyclohexyl)-4'-butoxybiphenyl
4-(4-cyano-4-heptylcyclohexyl)-4'-pentoxybiphenyl
4-(4-cyano-4-heptylcyclohexyl)-4'-hexoxybiphenyl
4-(4-cyano-4-heptylcyclohexyl)-4'-heptoxybiphenyl, m.p. 87°, c.p. 155°
4-(4-cyano-4-heptylcyclohexyl)-4'-octoxybiphenyl, m.p. 83°, c.p. 154°
4-(4-cyano-4-heptylcyclohexyl)-4'-nonoxybiphenyl, m.p. 81°, c.p. 152°
4-(4-cyano-4-octylcyclohexyl)-4'-ethylbiphenyl
4-(4-cyano-4-octylcyclohexyl)-4'-propylbiphenyl
4-(4-cyano-4-octylcyclohexyl)-4'-butylbiphenyl
4-(4-cyano-4-octylcyclohexyl)-4'-pentylbiphenyl, m.p. 52°, c.p. 124°
4-(4-cyano-4-octylcyclohexyl)-4'-hexylbiphenyl
4-(4-cyano-4-octylcyclohexyl)-4'-heptylbiphenyl, m.p. 61°, c.p. 122°
4-(4-cyano-4-octylcyclohexyl)-4'-octylbiphenyl, m.p. 65°, c.p. 125°
4-(4-cyano-4-octylcyclohexyl)-4'-nonylbiphenyl
4-(4-cyano-4-octylcyclohexyl)-4'-butoxybiphenyl
4-(4-cyano-4-octylcyclohexyl)-4'-pentoxybiphenyl
4-(4-cyano-4-octylcyclohexyl)-4'-hexoxybiphenyl
4-(4-cyano-4-octylcyclohexyl)-4'-heptoxybiphenyl, m.p. 85°, c.p. 151°
4-(4-cyano-4-octylcyclohexyl)-4'-octoxybiphenyl, m.p. 81°, c.p. 150°
4-(4-cyano-4-octylcyclohexyl)-4'-nonoxybiphenyl, m.p. 72°, c.p. 149°
4-(4-cyano-4-nonylcyclohexyl)-4'-ethylbiphenyl
4-(4-cyano-4-nonylcyclohexyl)-4'-propylbiphenyl
4-(4-cyano-4-nonylcyclohexyl)-4'-butylbiphenyl
4-(4-cyano-4-nonylcyclohexyl)-4'-pentylbiphenyl
4-(4-cyano-4-nonylcyclohexyl)-4'-heptylbiphenyl
4-(4-cyano-4-nonylcyclohexyl)-4'-octylbiphenyl
4-(4-cyano-4-nonylcyclohexyl)-4'-nonylbiphenyl
4-(4-cyano-4-nonylcyclohexyl)-4'-butoxybiphenyl
4-(4-cyano-4-nonylcyclohexyl)-4'-pentoxybiphenyl
4-(4-cyano-4-nonylcyclohexyl)-4'-hexoxybiphenyl
4-(4-cyano-4-nonylcyclohexyl)-4'-heptoxybiphenyl
4-(4-cyano-4-nonylcyclohexyl)-4'-octoxybiphenyl
4-(4-cyano-4-nonylcyclohexyl)-4'-nonoxybiphenyl
4'-octyloxybiphenyl-4-yl 4-cyano-4-heptylcyclohexanecarboxylate, m.p. 86°, c.p. 185°
p-(trans-4-propylcyclohexyl)phenyl 4-cyano-4-heptylcyclohexanecarboxylate, m.p. 84°, c.p. 153°
1-(1-cyano-4-heptylcyclohexyl)-2-(4'-octyloxybiphenyl-4-yl)ethane, m.p. 85°, c.p. 141°
4'-octyloxybiphenyl-4-yl 1-cyano-4-pentylcyclohexanecarboxylate, m.p. 53°, c.p. 149°
p-heptylphenyl-4-cyano-4-heptylcyclohexanecarboxylate, m.p. 38°, c.p. 56°
p-heptyloxyphenyl-4-cyano-4-heptylcyclohexanecarboxylate, m.p. 35°, c.p. 84°
4'-hexylbiphenyl-4-yl 1-cyano-4-pentylcyclohexanecarboxylate, m.p. 46°, c.p. 121°
1-cyano-1-pentyl-4-[4'-(trans-4-pentylcyclohexyl)biphenyl-4-yl]cyclohexane, m.p. 96°, c.p. 285°
p-(trans-4-propylcyclohexyl)phenyl 1-cyano-4-pentylcyclohexanecarboxylate, m.p. 79°, c.p. 114°
1-(trans-4-pentylcyclohexyl)-2-[1-cyano-4-(4'-heptyloxybiphenyl-4-yl)cyclohexyl]ethane, m.p. 100°, c.p. 251°
p-heptylphenyl p-(4-cyano-4-heptylcyclohexyl)benzoate, m.p. 88°, c.p. 138°

Especially preferred are optically active compounds of the formula I wherein one of the groups $R^1$ and $R^2$ denotes —O—$C_2H_4$—*CHCH$_3$—$C_3H_6$—CH(CH$_3$)$_2$ or —COO—$C_2H_4$—*CHCH$_3$—$C_3H_6$—CH(CH$_3$)$_2$.

These compounds, like the analogous compounds, are obtainable by an etherification or an esterification with dihydrocitronellol or its reactive derivatives. Particularly preferred are the optically active compounds
r-1-cyano-cis-4-[4'-(3,7-dimethyloctyloxy)biphenyl-4-yl]-1-pentylcyclohexane
r-1-cyano-cis-4-[4'-(3,7-dimethyloctyloxy)biphenyl-4-yl]-1-hexylcyclohexane
r-1-cyano-cis-4-[4'-(3,7-dimethyloctyloxy)biphenyl-4-yl]-1-heptylcyclohexane
r-1-cyano-cis-4-[4'-(3,7-dimethyloctyloxy)biphenyl-4-yl]-1-octylcyclohexane, m.p. 51°, c.p. 113°
r-1-cyano-cis-4-[4'-(3,7-dimethyloctyloxy)biphenyl-4-yl]-1-nonylcyclohexane
r-1-cyano-cis-4-[4'-(3,7-dimethyloctyloxy)biphenyl-4-yl]-1-decylcyclohexane
r-1-cyano-cis-4-[4'-(3,7-dimethyloctyloxycarbonyl)biphenyl-4-yl]-1-pentylcyclohexane
r-1-cyano-cis-4-[4'-(3,7-dimethyloctyloxycarbonyl)biphenyl-4-yl]-1-hexylcyclohexane
r-1-cyano-cis-4-[4'-(3,7-dimethyloctyloxycarbonyl)biphenyl-4-yl]-1-heptylcyclohexane
r-1-cyano-cis-4-[4'-(3,7-dimethyloctyloxycarbonyl)biphenyl-4-yl]-1-octylcyclohexane
r-1-cyano-cis-4-[4'-(3,7-dimethyloctyloxycarbonyl)biphenyl-4-yl]-1-nonylcyclohexane
r-1-cyano-cis-4-[4'-(3,7-dimethyloctyloxycarbonyl)biphenyl-4-yl]-1-decylcyclohexane All the compounds of formula I are prepared by methods known per se as they are described in the literature (e.g. in the standard works such as Houben-Weyl, Methoden der Organischen Chemie (Methods of Organic Chemistry), Georg-Thieme-Verlag, Stuttgart), or in the examples below and in particular under reaction conditions which are known and suitable for the reactions mentioned. At the same time use can also be made of variants known per se which are not mentioned in more detail here.

Formula I comprises compounds which are predominantly known such as the preferred compounds described in German Offenlegungsschriften Nos. 3,231,707, 3,319,781, 3,320,024, 3,407,013, 3,443,929, 3,332,690, 3,332,691, 3,332,692, 2,933,563, 2,853,728, 2,613,293, 3,401,320, 3,136,624, 3,040,632, 3,205,766, 2,240,864, 2,937,700, 3,410,734, 3,324,686, European Published Application No. 0,085,995, European Published Application No. 0,084,194, East German Pat. No. 116,732, French Pat. No. 2,425,469, French Pat. No. 2,419,966, U.S. Pat. No. 4,237,026, U.S. Pat. No.

3,953,491, U.S. Pat. No. 4,225,454, or in H. J. Deutscher et al., J. prakt. Chemie, 321, 569 (1979) and J. C. Dubois et al., Mol. Cryst. Liq. Cryst. 47, 193 (1978).

Preferred phases according to the invention contain at least one new compound of the formula II.

The present invention relates, however, equally to new compounds of the formula II

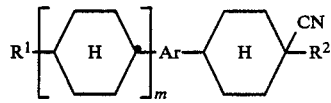

wherein $R^1$ and $R^2$ in each case denote a straight-chain alkyl group having 1 to 15 C atoms, wherein one or more nonadjacent $CH_2$ groups may also be replaced by —O—, —CO—, —O—CO—, —O—COO—, —CO—O—, —CHCH$_3$—, —CH=CH—, —CH-halogen and/or —CHCN—, m denotes 0 or 1, and Ar denotes 1,4-phenylene, 4,4'-biphenylyl or 2,6-naphthylene, wherein one or more CH groups may be replaced in each case by N.

The compounds of formula II have a high chemical stability. They are colourless and are readily miscible with all the usual liquid crystals. Their use in liquid-crystalline phases leads to wider mesophase ranges and improved values for the spontaneous polarization in chiral tilted smectic phases. The phases according to the invention are therefore very well suited for displays which are based on the principle of SSFLC technology. $R^1$ and $R^2$ preferably have the preferred meanings specified in the case of formula I.

Ar is preferably a group of the formula a to j:

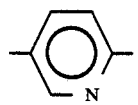

a

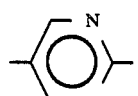

b

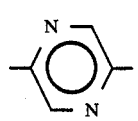

c

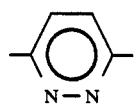

d

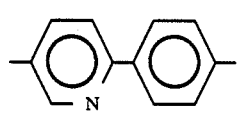

e

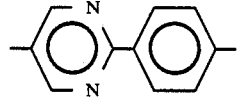

f

g

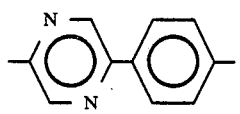

h

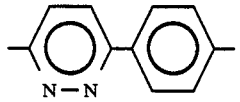

i

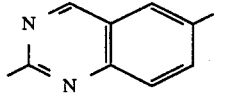

j

Groups of the formulae a, b, c, e, f, g and h are preferred. Especially preferred are e and f.

The compounds of formula II may, for example, be obtained by reacting corresponding cyclohexanecarbonitriles (formula II, $R^2$=H) with a halide of the formula $R^2$-halogen.

The nitrile is expediently first converted to the corresponding carbanion with a strong base such as NaH, NaNH$_2$, lithium diisopropylamide, lithium piperidide or lithium 2,5-diisopropylpiperidide or potassium tert-butylate, preferably in an inert solvent, for example a hydrocarbon such as toluene, an ether such as THF or dioxane, an amide such as DMF, a sulphoxide such as dimethylsulphoxide or a mixture of such solvents. After adding $R^2$-halogen the temperature is expediently held for 0.5 to 16 hours at temperatures between 0° and 150°.

The halides may be obtained, for example, from the corresponding alcohols. The halogen is preferably bromine or iodine.

The preferred meanings for groups in formula I apply analogously also for the compounds of formula II.

The present invention also relates to new optically active compounds of the formula I-A $$R^1-Q^1-A-(Q^2)_q-R^2 \qquad \text{I-A}$$

wherein $R^1$ and $R^2$ each denote independently of each other an alkyl group or a polyfluoroalkyl group containing 1 to 15 C atoms in each case, wherein one or more $CH_2$ groups or $CF_2$ groups may also be replaced by a grouping selected from the group comprising —O—, —S—, —CO—, —CHhalogen—, —CHCN—, —O—CO—, —O—COO—, —CO—O— and —CH=CH— or also by a combination of two suitable groupings, two hetero atoms not being directly linked to each other, and one of the radicals $R^1$ and $R^2$ also being halogen,

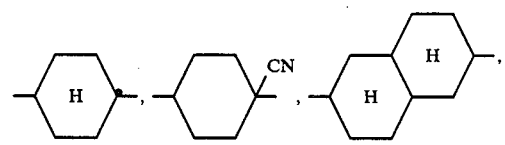

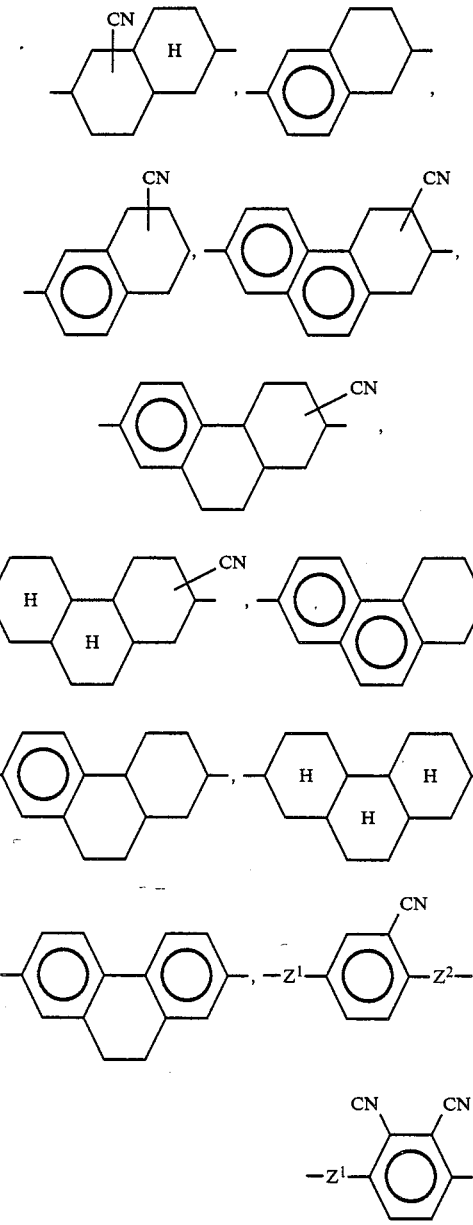

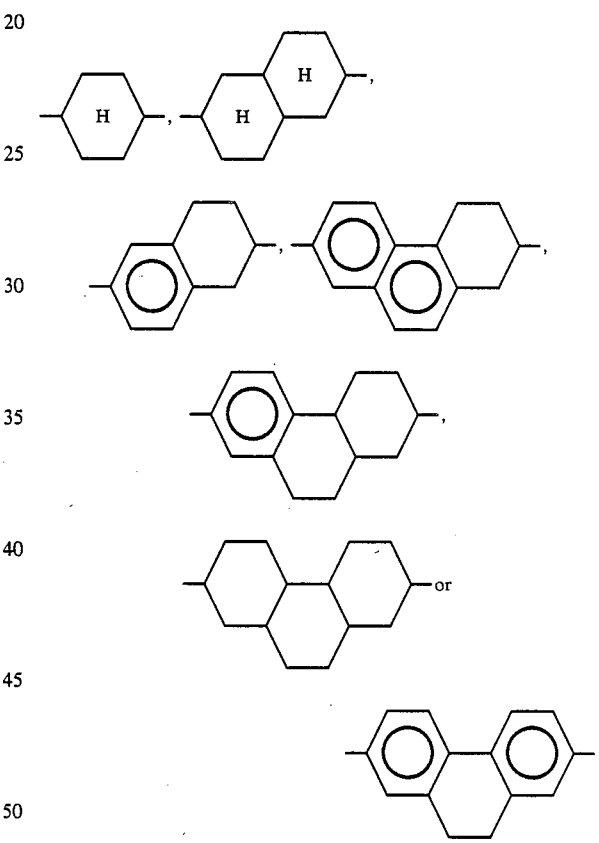

or one of these groups, wherein one or more $CH_2$ groups are replaced by O and/or S or aliphatic and/or aromatic CH groups are replaced by N, q denotes 0 or 1, $Q^1$ and $Q^2$ each denote independently of each other —$(A°—Z°)_p$—, where A° denotes unsubstituted 1,4-cyclohexylene or 1,4-cyclohexylene substituted singly or multiply by halogen atoms, $CH_3$ and/or nitrile groups, wherein one or two nonadjacent $CH_2$ groups may also be replaced by —O— and/or —S— and/or a

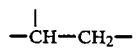

grouping may be replaced by

(Cy), or unsubstituted 1,4-phenylene or 1,4-phenylene substituted singly or multiply by halogen atoms, $CH_3$— and/or nitrile groups, wherein one or more CH groups may also be replaced by N (Ph), one of the radicals A° may also stand for 2,6-naphthylene (Na) or tetrahydro-2,6-naphthylene (4H-Na), optionally substituted by halogen or CN, $Z°$, $Z^1$ and $Z^2$ each denote independently of each other —CO—O—, —O—CO—, —$CH_2$O—, —O$CH_2$—, —$CH_2CH_2$—, —CHCN—$CH_2$—, —$CH_2$—CHCN— or a single bond, and p denotes 1, 2 or 3, or if A=tetra— or octahydrophenanthrene, also 0, and if A= at least one group Z° denotes —CHCN$CH_2$ or —$CH_2$CHCN— and/or in at least one of the groups $R^1$ and $R^2$ at least one $CH_2$ group or $CF_2$ group is replaced by —CHCN—, with the proviso that at least one of the groups $R^1$ and $R^2$ has the formula —O—Q°—alkyl or —CO—O—Q°—O—alkyl, wherein alkyl denotes an alkyl group containing 1 to 10 C atoms and Q° denotes —*CHCH_3—CO—, —CO—*CHCH_3—, —*CHCH_3—$CH_2$— or —$CH_2$—*CH_3—.

The compounds of the formula I-A have a high chemical stability. They are colourless and readily miscible with many common liquid crystals. Their use in liquid-crystalline phases results in wide or mesophase ranges and/or improved values for the spontaneous polarization in chiral tilted smectic phases. The phases according to the invention containing compounds of the formula I-A are therefore very well suited for displays which are based on the principle of SSFLC technology.

The compounds of the formula I-A can be prepared by known methods, as they are described in the literature (for example, in the standard works, such as Houben-Weyl, Methoden der Organischen Chemie, (Methods of organic chemistry), Georg-Thieme-Verlag, Stuttgart; European Published Application No. 0,175,591; WO 86/02938), and in particular under reaction conditions which are known and suitable for the required reactions (for example, an esterification or an etherification). At the same time use can also be made of variants known per se which are not mentioned in more detail here.

The preferred meanings for the radicals of formula I apply analogously also to the compounds of the formula I-A. Preferably, the compounds of the formula I-A contain at least one radical of the formula —O—*CHC-H$_3$—CO—O—alkyl. Alkyl is preferably a straight-chain alkyl group containing preferably 2 to 6 C atoms.

The invention relates further to new tetralincarbonitriles of the formula I'

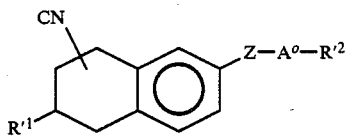

wherein
R'$^1$ denotes an alkyl group containing 1–15 C atoms, wherein one or more nonadjacent CH$_2$ groups may also be replaced by —O—, —O—CO—, —CO— and/or —CH=CH— (trans), or trans-4—R'$^1$—cyclohexyl,
Z denotes —CH$_2$CH$_2$—, —CO—O—, —O—CO—, —O—CH$_2$—, —CH$_2$O— or a single bond,
A° denotes unsubstituted 1,4-phenylene or 1,4-phenylene substituted by one or two halogen atoms, CH$_3$- and/or CN groups, wherein one or more CH groups may also be replaced by N, trans-1,4-cyclohexylene, wherein one or two nonadjacent CH$_2$ groups may also be replaced by —O— and/or —S—, 1,4-bicyclo[2.2.2]octylene or a single bond,
R'$^2$ denotes an alkyl group containing 1–15 C atoms, wherein one or more nonadjacent CH$_2$ groups may also be replaced by —O—, —O—CO—, —CO— and/or —CH=CH—(trans), F, Cl, Br, CN or, provided at least one of the groups Z and A° does not stand for a single bond, also H,
it being possible for one or more CH groups in the aromatic ring also to be replaced by N and/or for one or two nonadjacent CH$_2$ groups in the hydrogenated ring to be replaced by O and/or S.

For the sake of simplicity "Phe" hereinafter denotes a 1,4-phenylene group, "Cyc" a 1,4-cyclohexylene group, "Dio" a 1,3-dioxane-2,5-diyl group, "Bi" a bicyclo[2.2.2]octylene group, "Pyr" a pyrimidine-2,5-diyl group and "Tet" the group

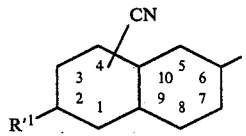

Similar compounds are known, for example, from German Offenlegungsschrift No. 3,319,781. However, the compounds specified there, in contrast to the present compounds, contain a perhydrogenated decalin system.

Like similar compounds, the compounds of the formula I' can be used as components for liquid crystal dielectrics, in particular for displays which are based on the principle of the twisted cell, the principle of the SSFLC technology, the guest-host effect, the effect due to the deformation of aligned phases, or the dynamic scattering effect.

The invention was based on the object of finding new stable liquid-crystalline or mesogenic compounds which are suitable as components of liquid-crystalline dielectrics. This object was solved by providing the compounds of formula I'.

It was found that the compounds of the formula I' are excellently suitable as components of liquid-crystalline dielectrics. In particular, they can be used to prepare stable liquid-crystalline phases with strongly negative dielectric anisotropy and consequently small threshold or control voltage for electrooptical effects and comparatively low viscosity.

In addition, with the provision of compounds of formula I' the range of liquid-crystalline substances which are suitable for the preparation of nematic mixtures considered from the point of view of different applications is quite generally substantially widened.

The compounds of formula I' have a wide field of application. Depending on the selection of substituents these compounds may serve as basic materials from which liquid-crystalline dielectrics are predominantly made up; liquid-crystalline basic materials from other compound categories, however, may also be added to the compounds of formula I' in order, for example, to reduce the dielectric and/or optical anisotropy of such a dielectric. The compounds of formula I' are further suitable as intermediate products for the preparation of other substances which may be used as components of liquid-crystalline dielectrics.

The compounds of formula I' are colourless in the pure state and form liquid-crystalline mesophases in a temperature range which is favourably situated for electrooptical use. They are very stable chemically, thermally and against light.

The subject of the invention is therefore formed by the compounds of the formula I' and also a process for their preparation which is characterized in that a compound, which in other respects corresponds to the formula I' but contains one or more reducible groups and/or C—C bonds in place of H atoms, is treated with a reducing agent, or that HCN is attached to a compound which in other respects corresponds to the formula I, but does not contain a CN group in the tetralin radical but an additional double bond, or that in order to prepare esters of formula I' (wherein Z denotes —CO—O— or —O—CO— or wherein R'$^2$ denotes —O—CO—alkyl or —COO—alkyl), a corresponding carboxylic acid or one of its reactive derivatives is reacted with a corresponding alcohol or one of its reactive derivatives, or that, in order to prepare dioxane derivatives of the formula I' (wherein A° denotes 1,3-dioxane-2,5-diyl), a corresponding aldehyde is reacted with a suitable diol, or that a suitable carboxylic acid amide is dehydrated or a suitable carboxylic acid halide is reacted with sulphamide or a suitable chloro or bromo compound is reacted with a cyanide, or that, in order to prepare tetralin-2-carbonitrile of the formula I', a nitrile of the formula II'

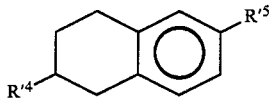
II' wherein
R'⁴ denotes CN and R'⁵ denotes —Z—A°—R'² and A°, Z and R'² have the specified meanings, is reacted with a compound of the formula III'

Q-X'  III' wherein
Q denotes R'¹ and
X' denotes Cl, Br, I, OH or a reactive esterified OH group
and R'¹ has the specified meanings,
or that a compound which corresponds to the formula I' but contains in place of a C—C bond between the C atom carrying the CN group and a C atom adjacent to it an additional H atom (on the C atom carrying the CN group) and an additional X' group (on the C atom adjacent to it, X' having the specified meaning), is cyclized with the elimination of HX', or that, in order to prepare ethers of formula I' (wherein R'¹ and/or R'² denote alkyl chains wherein up to 2 CH₂ groups are replaced by O atoms and/or Z is an —OCH₂— or —CH₂O group), a corresponding hydroxy compound is etherified.

The subject of the invention is moreover formed by the use of the compounds of formula I' as components of liquid-crystalline dielectrics. The subject of the invention is furthermore formed by liquid-crystalline dielectrics having a content of at least one compound of the formula I' and also electrooptical display elements which contain such dielectrics.

Above and below A°, Q, R'¹, R'², R'⁴, R'⁵, X' and Z have the specified meaning provided nothing else is expressly noted.

The compounds of formula I' consequently cover compounds of the partial formulae I'a to I'jj:

| | |
|---|---|
| Tet—CH₂CH₂—Phe—R'² | I'a |
| Tet—CH₂CH₂—Cy—R'² | I'b |
| Tet—CH₂CH₂—Dio—R'² | I'c |
| Tet—CH₂CH₂—Bi—R'² | I'd |
| Tet—CH₂CH₂—Pyr—R'² | I'e |
| Tet—CH₂CH₂—R'² | I'f |
| Tet—CO—O—Phe—R'² | I'g |
| Tet—CO—O—Cy—R'² | I'h |
| Tet—CO—O—Dio—R'² | I'i |
| Tet—CO—O—Bi—R'² | I'j |
| Tet—CO—O—Pyr—R'² | I'k |
| Tet—CO—O—R'² | I'l |
| Tet—O—CO—Phe—R'² | I'm |
| Tet—O—CO—Cy—R'² | I'n |
| Tet—O—CO—Dio—R'² | I'o |
| Tet—O—CO—Bi—R'² | I'p |
| Tet—O—CO—Pyr—R'² | I'q |
| Tet—O—CO—R'² | I'r |
| Tet—O—CH₂—Phe—R'² | I's |
| Tet—O—CH₂—Cy—R'² | I't |
| Tet—O—CH₂—Dio—R'² | I'u |
| Tet—O—CH₂—Bi—R'² | I'v |
| Tet—O—CH₂—Pyr—R'² | I'w |
| Tet—O—CH₂—R'² | I'x |
| Tet—CH₂—O—Phe—R'² | I'y |
| Tet—CH₂—O—Cy—R'² | I'z |
| Tet—CH₂—O—Dio—R'² | I'aa |
| Tet—CH₂—O—Bi—R'² | I'bb |
| Tet—CH₂—O—Pyr—R'² | I'cc |
| Tet—CH₂—O—R'² | I'dd |
| Tet—Phe—R'² | I'ee |
| Tet—Cy—R'² | I'ff |
| Tet—Dio—R'² | I'gg |
| Tet—Bi—R'² | I'hh |
| Tet—Pyr—R'² | I'ii |
| Tet—R'². | I'jj |

(In I'jj, R'² is not identical to H.) Z is preferably a single bond. A° is preferably a single bond or Cy. Compounds of the formula I'ff and I'jj are consequently preferred.

In the tetralin system the CN group is preferably on the tertiary C atom or in the 1-position; it may however also be in the 3- or 4-position.

In the compounds of the formula above and below R'¹ and R'² preferably denote alkyl, furthermore alkoxy (in particular if said radicals are on a Phe group) or another oxaalkyl group.

X' is preferably Cl or Br, but also I, OH or reactively esterified OH such as alkylsulphonyloxy containing in particular 1–6 C atoms (e.g. methylsulphonyloxy) or arylsulphonyloxy containing in particular 6–10 C atoms (e.g. phenylsulphonyloxy, p-tolylsulphonyloxy or naphthylsulphonyloxy).

In the compounds of the formulae above and below the alkyl radicals, in which one ("alkoxy" or "oxaalkyl") or two ("alkoxyalkoxy" or "dioxaalkyl") CH₂ groups may be replaced by O atoms, may be straigthchain or branched. Preferably they are straight-chain, contain 2, 3, 4, 5, 6, 7, 8, 9 or 10 C atoms and consequently preferably denote ethyl, propyl, butyl, pentyl, hexyl, heptyl, octyl, nonyl, decyl, ethoxy, propoxy, butoxy, pentoxy, hexoxy, heptoxy, octoxy, nonoxy, decoxy, 2-oxapropyl (=methoxymethyl), 2-(=ethoxymethyl) or 3-oxabutyl (=2-methoxyethyl), 2-, 3- or 4-oxapentyl, 2-, 3-, 4-or 5-oxahexyl, 2-, 3-, 4-, 5- or 6-oxaheptyl, also methyl, methoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formulae I' and also I'a to I'jj having branched wing groups R'¹ or R'² may occasionally be of importance because of a better solubility in the usual liquid-crystalline basic materials, in particular, however, as chiral dopants if they are optically active. Branched groups of this type as a rule contain one chain branching.

Preferred branched radicals R'¹ and R'² are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

Of the compounds of formula I' and also I'a to I'z those are preferred in which at least one of the radicals contained therein has one of the specified preferred meanings and/or wherein the CN group is in one of the specified preferred positions. Especially preferred smaller groups of compounds are those of the formulae I'kk and I'll:

Tet-alkyl                                   I'kk

Tet-Cy-alkyl                              I'll

At the same time those stereoisomers of trans-tetralin are preferred in which the groups R'¹ and —Z—A-°—R'² are equatorial and the CN group axial.

Those of the abovementioned formulae which contain one of the groups Dio or Pyr encompass in each case the two possible 2,5- or 1,4-position isomers. Thus, the partial formula I'gg encompasses, for example, the 2-Tet-5-R'²-1,3-dioxanes and the 2-R'²-5-Tet-1,3-dioxanes, and the partial formula I'ii the 2-Tet-5-R'²-pyrimidines and the 2-R'²-5-Tet-pyrimidines.

The compounds of formula I' may be prepared by methods known per se such as are described in the literature (e.g. in the standard works such as Houben-Weyl, Methoden der Organischen Chemie (Methods of Organic Chemistry), Georg-Thieme-Verlag, Stuttgart), and in particular using the reaction conditions which are known and suitable for the reactions mentioned. At the same time use may also be made of variants known per se which are not mentioned in more detail here.

If desired, the starting substances can also be formed in situ in a manner such that they are not isolated from the reaction mixture but are immediately converted further into compounds of formula I'.

Thus, the compounds of formula I' can be prepared by reducing a compound which in other respects corresponds to formula I' but contains one or more reducible groups and/or C—C bonds instead of H atoms.

As reducible groups carbonyl groups are preferably suitable, in particular keto groups, but also, for example, free or esterified hydroxy groups or aromatically bound halogen groups. Preferred starting substances for the reduction correspond to formula I', but may contain instead of the tetralin ring a naphthalene or dihydronaphthalene ring or a dihydronaphthalinone ring or, instead of a cyclohexane ring, a cyclohexene ring or cyclohexanone ring and/or, instead of a —CH₂CH₂ group, a —CH=CH— group or a —CH₂CO— group.

The reduction takes place under conditions in which the CN group remains intact, expediently by catalytic hydrogenation at temperatures between about 0° and about 100° and pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Expediently, noble metals such as Pt or Pd, which can be used in the form of oxides (e.g. PtO₂, PdO), on a carrier (e.g. Pd on charcoal, calcium carbonate or strontium carbonate) or in finely dispersed form, are suitable as catalysts.

Compounds of the formula I' can furthermore be obtained by adding hydrogen cyanide to a corresponding dihydronaphthalene derivative (which in other respects corresponds to the formula I', but does not contain a CN group in the tetralin radical but an additional double bond instead).

This addition is achieved, for example, in the presence of an inert solvent, for example a halogenated hydrocarbon such as CH₂Cl₂ or CHCl₃, a nitrile such as acetonitrile or an amide such as dimethylformamide (DMF) at temperatures between about −10° and +150° and pressures between about 1 and 100 bar. An addition of catalysts may be favourable, for example, an HCN addition may be catalyzed by adding bis[2,3-O-isopropylidene-2,3-dihydroxy-1,4-bis(diphenylphosphino)butane] palladium.

Esters of the formula I' (Z=—CO—O— or —O—CO— or R'²=—O—CO—alkyl or —COO—alkyl) can also be obtained by esterifying corresponding carboxylic acids of the formulae Tet—COOH, R'²—A°—COOH or Tet—Z—A°—COOH (or their reactive derivatives) with alcohols or phenols of the formulae R'²—A°—OH, Tet—OH or Tet—Z—A°—OH (or their reactive derivatives).

In particular the acid halides, especially the chlorides and bromides, also the anhydrides, for example also mixed anhydrides of the formulae Tet—CO—O—CO—CH₃, R'²—A°—CO—O—CO—CH₃ and Tet—Z—A°—CO—O—CO—CH₃, and azides or esters, in particular alkyl esters containing 1–4 C atoms in the alkyl group are suitable as reactive derivatives of the carboxylic acids mentioned.

In particular the corresponding metal alcoholates or phenolates of the formulae R'²—A—OM, Tet—OM and Tet—Z—A°—OM, wherein M denotes one equivalent of a metal, preferably an alkali metal such as Na or K, are suitable as reactive derivatives of the alcohols or phenols mentioned.

The esterification is advantageously carried out in the presence of an inert solvent. Well suited are in particular ethers such as diethyl ether, di-n-butyl ether, THF, dioxane or anisole, ketones such as acetone, butanone or cyclohexanone, amides such as DMF or phosphoric acid hexamethyltriamide, hydrocarbons such as benzene, toluene or xylene, halogenated hydrocarbons such as carbon tetrachloride or tetrachloroethylene and sulphoxides such as dimethylsulphoxide or sulpholane. Solvents which are not miscible with water may simultaneously be advantageously used for distilling off the water formed in the esterification azeotropically. Occasionally an excess of an organic base, for example pyridine, quinoline or triethylamine may be used as the solvent for the esterification. The esterification may also be carried out in the absence of a solvent, for example by simply heating the components in the presence of sodium acetate. The reaction temperature is usually between −50° and +250°, preferably between −20° and +80°. At these temperatures the esterification reactions are as a rule complete after 15 minutes to 48 hours.

In detail, the reaction conditions for the esterification depend substantially on the nature of the starting substances used. Thus, a free carboxylic acid is reacted with a free alcohol or phenol, as a rule in the presence of a strong acid, for example a mineral acid such as hydrochloric or sulphuric acid. A preferred method of reaction is the reaction of an acid anhydride or, in particular, an acid chloride with an alcohol, preferably in a basic medium, in particular alkalimetal hydroxides such as sodium or potassium hydroxide, alkalimetal carbonates or alkalimetal hydrogencarbonates such as sodium carbonate, sodium hydrogencarbonate, potassium carbonate or potassium hydrogencarbonate, alkalimetal acetates such as sodium or potassium acetate, alkaline earth metal hydroxides such as calcium hydroxide or organic bases such as triethylamine, pyridine, lutidine, collidine or quinoline being of importance as bases. A further preferred embodiment of the esterification is first to convert the alcohol or the phenol into the sodium or potassium alcoholate or phenolate, for example by treating with ethanolic sodium or potassium hydroxide, isolating the alcoholate or phenolate and suspending it together with sodium hydrogencarbonate or potassium carbonate while stirring in acetone or diethyl ether and adding a solution of the acid chloride or anhydride in diethyl ether, acetone or DMF to this suspension, expediently at temperatures between about $-25°$ and $+20°$.

Dioxane derivatives of the formula I (wherein the group A* denotes a 1,3-dioxane-2,5-diyl group) are expediently prepared by reacting a corresponding aldehyde of the formula Tet—Z—CHO or R'$^2$—CHO (or one of its reactive derivatives) with a corresponding 1,3-diol of the formula R'$^2$—CH(CH$_2$OH)$_2$ or Tet—Z—CH(CH$_2$OH)$_2$ (or one of its reactive derivatives), preferably in the presence of an inert solvent such as benzene or toluene and/or of a catalyst, for example a strong acid such as sulphuric acid, benzenesulphonic acid or p-toluenesulphonic acid, at temperatures between about 20° and about 150°, preferably between 80° and 120°. In particular acetals, for example of the formulae Tet—Z—CH(OR$^6$)$_2$, R'$^2$—CH(OR$^6$)$_2$, R'$^2$—CH(CH$_2$)$_2$—CHR$^7$ or Tet—Z—CH(CH$_2$O)$_2$—CHR$^7$, wherein R$^6$ denotes alkyl containing 1–4 C atoms, two radicals R$^6$ together also denote alkylene containing 2 or 3 C atoms and R$^7$ denotes H, alkyl containing 1–4 C atoms or phenyl, are suitable as reactive derivatives of the starting substances.

Some of the aldehydes and 1,3-diols mentioned, and also their reactive derivatives are known, some of them can be prepared without difficulty by standard methods of organic chemistry from compounds known from the literature. For example, the aldehydes can be obtained by oxidation of corresponding alcohols or by reduction of corresponding carboxylic acids or their derivatives, and the diols by reduction of corresponding diesters.

For the preparation of nitriles of the formula I' corresponding acid amides in which there is a CONH$_2$ group instead of the CN group may be dehydrated. The amides may, for example, be obtained from corresponding esters or acid halides by reaction with ammonia. Inorganic acid chlorides such as SOCl$_2$, PCl$_3$, PCl$_5$, POCl$_3$, SO$_2$Cl$_2$, COCl$_2$, also P$_2$O$_5$, AlCl$_3$ (for example as a double compound with NaCl), aromatic sulphonic acids and sulphonic acid halides are, for example, suitable as water eliminating means. In this connection temperatures between about 0° and 150° may be employed in the presence or absence of an inert solvent; bases such as pyridine or triethylamine, aromatic hydrocarbons such as benzene, toluene or xylene or amides such as DMF are, for example, suitable as solvents.

In order to prepare the nitriles of the formula I', corresponding acid halides, preferably the chlorides may also be reacted with sulphamide, expediently in an inert solvent such as tetramethylenesulphone at temperatures between about 80° and 150°, preferably at 120°. After the usual working up the nitriles can be isolated directly.

For the preparation of nitriles of formula I' a corresponding chloro or bromo compound may also be reacted with a cyanide, expediently with a metal cyanide such as NaCN, KCN or Cu$_2$(CN)$_2$, for example in the presence of pyridine in an inert solvent such as DMF or N-methylpyrrolidone at temperatures between 20° and 200°.

The preferred nitriles of formula I' in which the nitrile group is in the 2-position can preferably also be obtained by reaction of nitriles of formula II' with compounds of formula III'. The nitriles of formula II' can be obtained, for example, from corresponding halides (corresponding to formula II', but Cl or Br instead of CN) and metal cyanides or from the corresponding ketones (tetralones) as described by J. Jiricny, D. M. Orere and C. B. Reese, J. Chem. Soc. Perk. I, 1487 (1980), the compounds of formula III' (insofar as they are not known), by reduction of the corresponding carboxylic esters to the corresponding hydroxy compounds (III', X'=OH) and also, if required, by reaction of the same with inorganic halides such as SOCl$_2$, HBr or HI; of the compounds of formula III' those are preferred in which Q denotes alkyl, R'$^2$—Cy— or R'$^2$—A*—CH$_2$CH$_2$—. The nitrile II' is expediently first converted to the corresponding carbanion with a strong base such as NaH, NaNH$_2$, lithium diisopropylamide, lithium piperidide or lithium 2,5-diisopropylpiperidide or potassium tert-butylate, preferably in an inert solvent, for example a hydrocarbon such as toluene, an ether such as THF or dioxane, an amide such as DMF, a sulphoxide such as dimethylsulphoxide or a mixture of such solvents. After adding III' (wherein X' differs from OH) the temperature is expediently kept for 0.5 to 16 hours at temperatures between $-30°$ and 100°. A reaction of II' with III' (X'=OH), on the other hand, is expediently achieved in the presence of azodicarboxylic acid esters/triphenylphosphine in THF at temperatures between about $-30°$ and $+30°$.

In a quite analogous manner nitriles of the formula I' can be obtained by "intramolecular alkylation" by cyclizing a nitrile which corresponds to the formula I', but contains, instead of a C—C bond between the C atom carrying the CN group and a C atom adjacent to this group, an additional H atom (on the C atom carrying the CN group) and an additional group X' (on the C atom adjacent to it) with HX' being eliminated.

Ethers of the formula I' (wherein R'$^1$ and/or R'$^2$ denote alkyl chains, wherein up to two CH$_2$ groups are replaced by O atoms and/or wherein Z is an —OCH$_2$— or a —CH$_2$O— group) can be obtained by etherification of corresponding hydroxy compounds, preferably corresponding phenols, the hydroxy compounds expediently first being converted into a corresponding metal derivative, for example by treatment with NaOH, KOH, Na$_2$CO$_3$ or K$_2$CO$_3$ into the corresponding alkalimetal alcoholate or alkalimetalphenolate. This can then be reacted with the corresponding alkyl halide, alkyl-sulphonate or dialkylsulphonate, expediently in an inert solvent such as acetone, DMF or dimethylsulphoxide or also an excess of aqueous or aqueous/alcoholic NaOH or KOH at temperatures between about 20° and 100°.

The following synthesis paths are especially preferred for the preparation of compounds of formula I'.

Synthesis path 1:

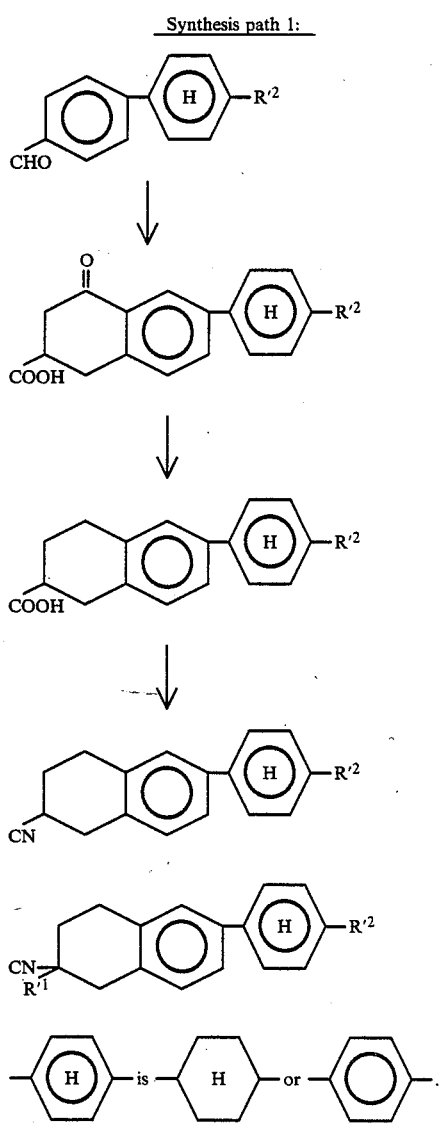

Compounds (2) are obtained from (1) by Stobbe condensation followed by reduction and by ring closure as described by W. S. Johnson et al., Org. Reactions 6, 2 (1954).

After reduction of the keto group (3) and conversion of the carboxylic acid group into the nitrile group (4), alkylation is carried out and the final product (5) is obtained.

Synthesis path 2:

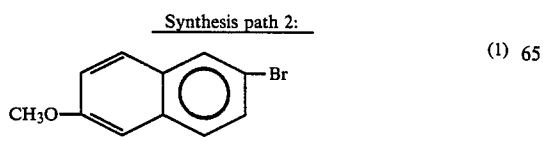

-continued
Synthesis path 2:

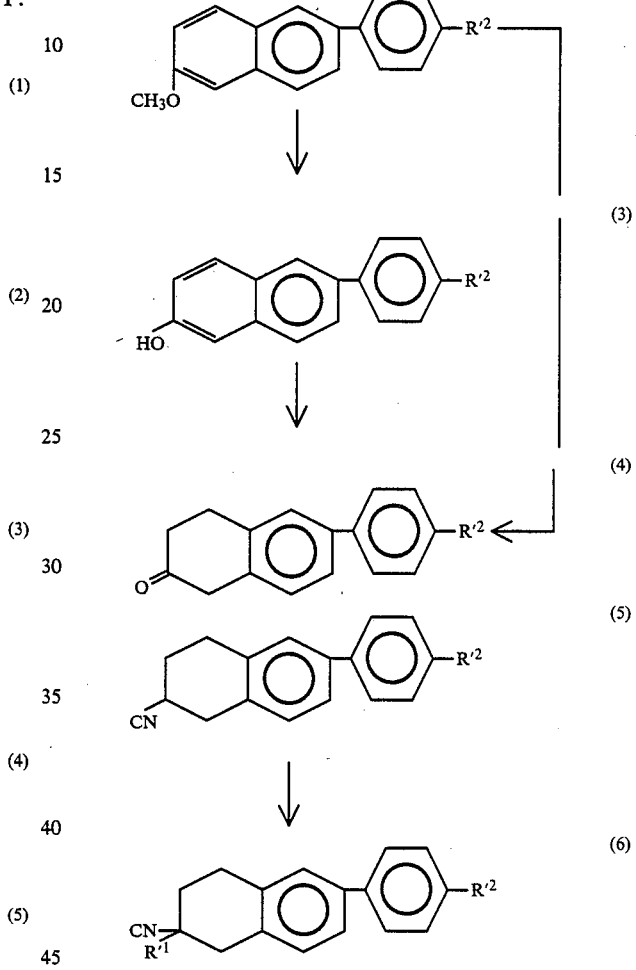

Compound (2) which can be obtained by the reaction of (1) with (1a) as described by Negishi et al., J. Org. Chem. 42, 1821 (1977), is reacted via the hydroxy compound (3) or analogously to the specification in Org. Synth. Coll., Volume IV, 903 directly to form the compound (4).

The ketone (4) is reacted as described by D. M. Orere and C. B. Reese in JCS. Chem. Comm. 280, 1977 with potassium cyanide and 2,4,6-triisopropylbenzenesulphonic acid hydrazide to form (5). The final product (6) is obtained by alkylation.

Synthesis path 3:

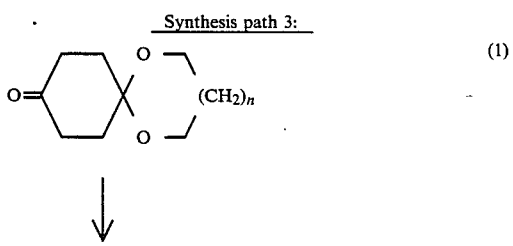

-continued
Synthesis path 3:

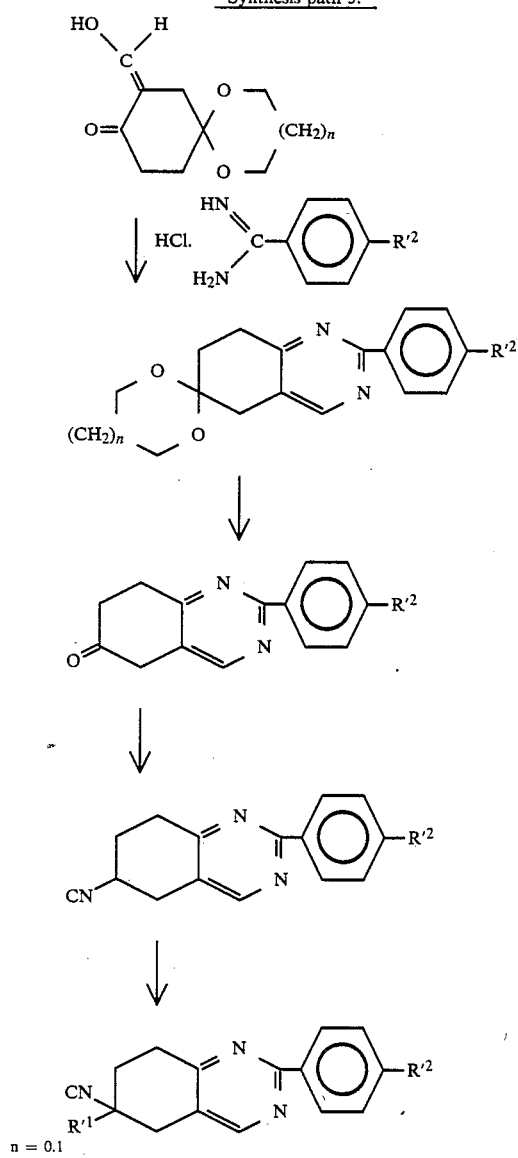

n = 0.1

1,4-Cyclohexanedione monoethylene ketal or 1,4-cyclohexanedione monopropylene ketal is reacted with ethyl formate in the presence of a base to form (2). By condensing with (2a) compounds (3) are obtained and the ketone (4) is subsequently obtained by splitting the spiro compound. The final product (6) is accessible in an analogous manner to synthesis path 2 [cf. compounds (4)–(6)].

The dielectrics according to the invention consist of 2 to 15, preferably 3 to 12 components, including at least one compound of the formula I'. The other constituents are preferably chosen from the nematic or nematogenic substances, in particular the known substances from the categories of the azoxybenzenes, benzylideneanilines, biphenyls, terphenyls, phenyl or cyclohexylbenzoates, phenyl or cyclohexyl cyclohexanecarboxylate, phenylcyclohexanes, cyclohexylbiphenyls, cyclohexylcyclohexanes, cyclohexylnaphthalenes, 1,4-bis(cyclohexylbenzenes), 4,4'-biscyclohexylbiphenyls, phenyl- or cyclohexylpyrimidines, phenyl- or cyclohexyldioxanes, optionally halogenized stilbenes, benzyl phenyl ether, tolanes and substituted cinnamic acids.

The phases according to the invention contain preferably at least two, in particular at least three compounds of formula I. Especially preferred are chiral tilted smectic liquid-crystalline phases according to the invention, whose achiral basic mixture contains, in addition to compounds of formula I, at least one other component with negative dielectric anisotropy or positive dielectric anisotropy which is small in value. This (these) other component(s) of the chiral basic mixture may make up 1 to 50%, preferably 10 to 25%, of the basic mixture. As further components with positive dielectric anisotropy which is small in value or negative anisotropy compounds of the partial formulae Va to Vp are suitable:

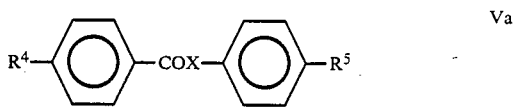
Va

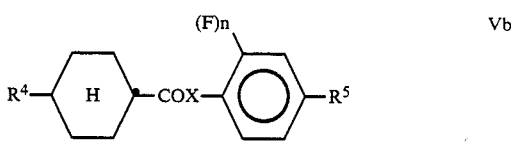
Vb

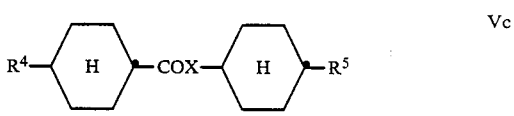
Vc

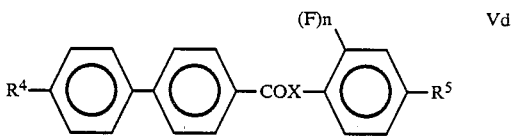
Vd

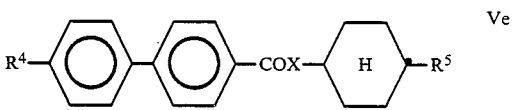
Ve

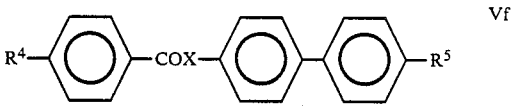
Vf

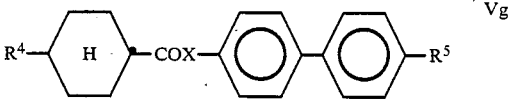
Vg

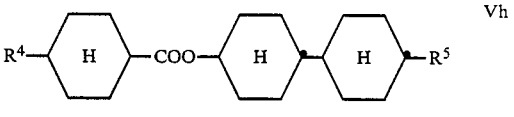
Vh

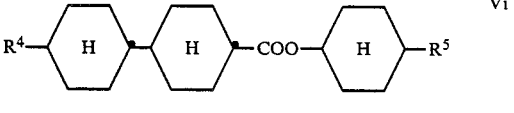
Vi

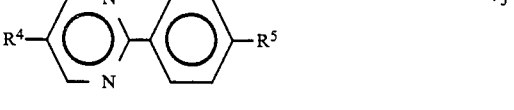
Vj

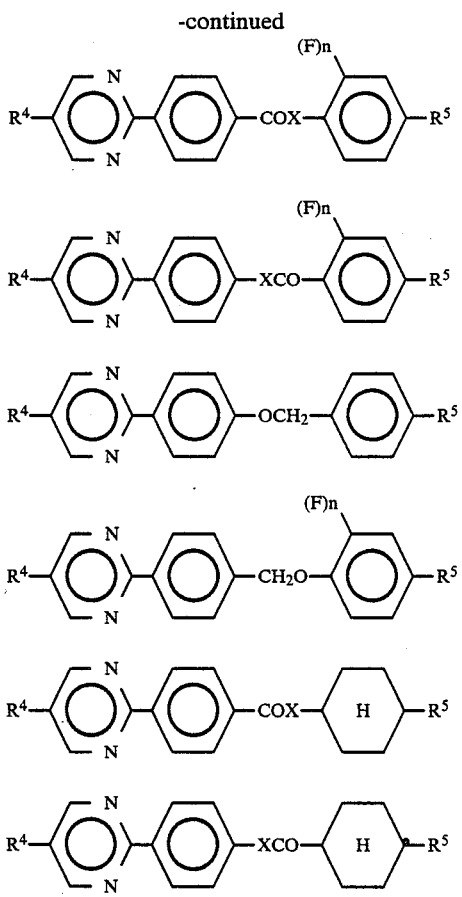

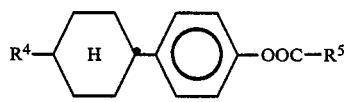

$R^4$ and $R^5$ are in each case preferably straight-chain alkyl, alkoxy, alkanoyloxy or alkoxycarbonyl, each containing 3 to 12 C atoms. X is preferably O. n is 0 or 1.

Especially preferred are the compounds of the partial formulae Va, Vb, Vd and Vf, wherein $R^4$ and $R^5$ each denote straight-chain alkyl or alkoxy, each containing 5 to 10 C atoms.

The compounds of partial formulae Vc, Vh and Vi are suitable as additives for lowering the melting point and are normally added to the basic mixtures in an amount of not more than 5%, preferably 1 to 3%. In the compounds of the partial formulae Vc, Vh and Vi $R^4$ and $R^5$ preferably denote straight-chain alkyl containing 2 to 7, preferably 3 to 5, C atoms. A further compound class suitable for lowering the melting point in the phases according to the invention is that of the formula wherein $R^4$ and $R^5$ have the preferred meaning specified for Vc, Vh and Vi.

In addition, compounds containing the structural element B or C are suitable as further components with negative dielectric anisotropy.

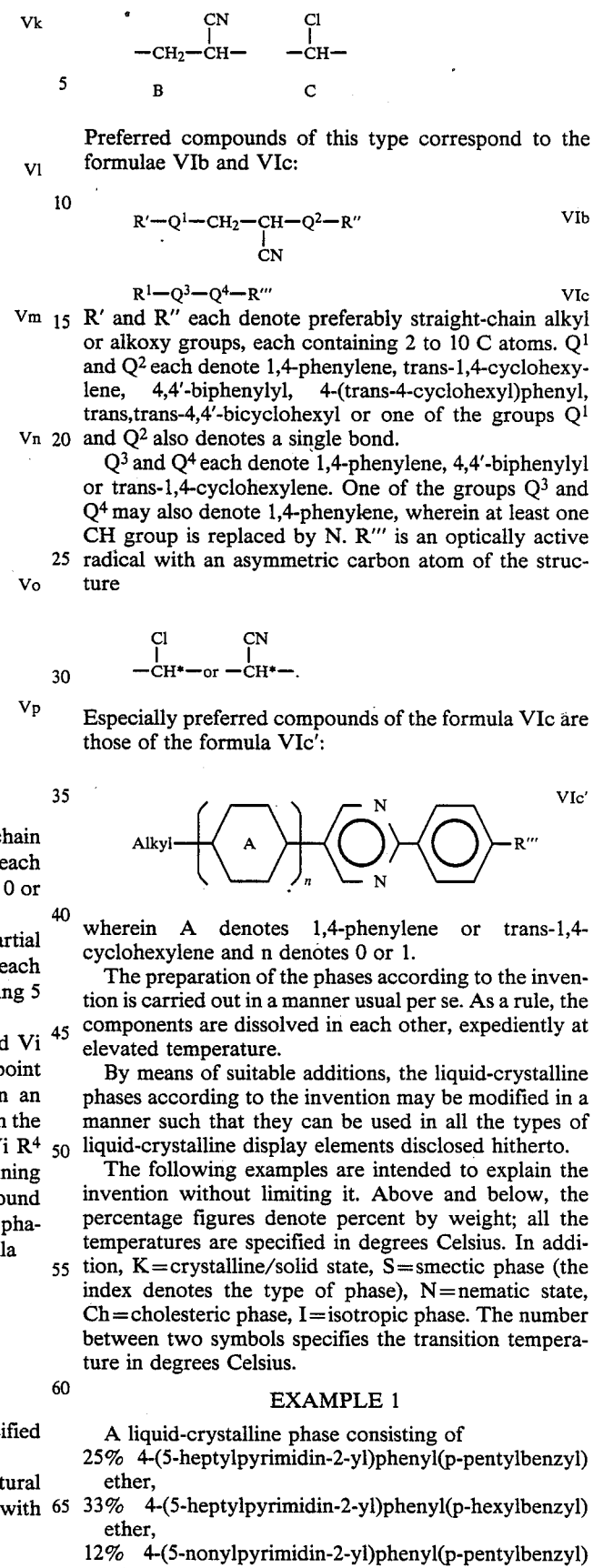

Preferred compounds of this type correspond to the formulae VIb and VIc:

$$R'—Q^1—CH_2—\underset{\underset{CN}{|}}{CH}—Q^2—R''  \quad \text{VIb}$$

$$R^1—Q^3—Q^4—R''' \quad \text{VIc}$$

R' and R'' each denote preferably straight-chain alkyl or alkoxy groups, each containing 2 to 10 C atoms. $Q^1$ and $Q^2$ each denote 1,4-phenylene, trans-1,4-cyclohexylene, 4,4'-biphenylyl, 4-(trans-4-cyclohexyl)phenyl, trans,trans-4,4'-bicyclohexyl or one of the groups $Q^1$ and $Q^2$ also denotes a single bond.

$Q^3$ and $Q^4$ each denote 1,4-phenylene, 4,4'-biphenylyl or trans-1,4-cyclohexylene. One of the groups $Q^3$ and $Q^4$ may also denote 1,4-phenylene, wherein at least one CH group is replaced by N. R''' is an optically active radical with an asymmetric carbon atom of the structure $$-\underset{\underset{Cl}{|}}{CH^*}- \text{ or } -\underset{\underset{CN}{|}}{CH^*}-.$$

Especially preferred compounds of the formula VIc are those of the formula VIc':

wherein A denotes 1,4-phenylene or trans-1,4-cyclohexylene and n denotes 0 or 1.

The preparation of the phases according to the invention is carried out in a manner usual per se. As a rule, the components are dissolved in each other, expediently at elevated temperature.

By means of suitable additions, the liquid-crystalline phases according to the invention may be modified in a manner such that they can be used in all the types of liquid-crystalline display elements disclosed hitherto.

The following examples are intended to explain the invention without limiting it. Above and below, the percentage figures denote percent by weight; all the temperatures are specified in degrees Celsius. In addition, K=crystalline/solid state, S=smectic phase (the index denotes the type of phase), N=nematic state, Ch=cholesteric phase, I=isotropic phase. The number between two symbols specifies the transition temperature in degrees Celsius.

EXAMPLE 1

A liquid-crystalline phase consisting of
25% 4-(5-heptylpyrimidin-2-yl)phenyl(p-pentylbenzyl) ether,
33% 4-(5-heptylpyrimidin-2-yl)phenyl(p-hexylbenzyl) ether,
12% 4-(5-nonylpyrimidin-2-yl)phenyl(p-pentylbenzyl) ether, 3% 4-(5-nonylpyrimidin-2-yl)phenyl(p-hexylbenzyl) ether,
21% 2-p-nonyloxyphenyl-5-nonylpyrimidine,
3% 2,3-dicyano-1,4-bis(trans-4-propylcyclohexylcarboxy)benzene and
3% 2,3-dicyano-1,4-bis(trans-4-pentylcyclohexylcarboxy)benzene has K/Sc 7°, Sc/N 64°, N/I 95.5° and a dielectric anisotropy $\Delta\epsilon$ of −0.5.

EXAMPLE 2

A liquid-crystalline phase consisting of
20% 4-(5-heptylpyrimidin-2-yl)phenyl(p-pentylbenzyl) ether,
27% 4-(5-heptylpyrimidin-2-yl)phenyl(p-hexylbenzyl) ether,
8% 4-(5-nonylpyrimidin-2-yl)phenyl(p-pentylbenzyl) ether,
4% 4-(5-nonylpyrimidin-2-yl)phenyl(p-propylbenzyl) ether,
24% 2-p-nonyloxyphenyl-5-nonylpyrimidine,
4% 2,3-dicyano-1,4-bis(trans-4-propylcyclohexylcarboxy)benzene,
7% 2,3-dicyano-1,4-bis(trans-4-propoxycyclohexylcarboxy)benzene and
6% 2,3-dicyano-1-(trans-4-butoxycyclohexylcarboxy)-4-(trans-4-hexoxycyclohexylcarboxy)benzene has K/Sc 12°, Sc/N 73°, N/I 104° and $\Delta\epsilon$ of −1.0.

EXAMPLE 3

A liquid-crystalline phase consisting of
20% 4-(5-heptylpyrimidin-2-yl)phenyl(p-pentylbenzyl) ether,
20% 4-(5-heptylpyrimidin-2-yl)phenyl(p-hexylbenzyl) ether,
4% 4-(5-nonylpyrimidin-2-yl)phenyl(p-pentylbenzyl) ether,
4% 4-(5-nonylpyrimidin-2-yl)phenyl(p-propylbenzyl) ether,
15% 4-(5-octylpyrimidin-2-yl)phenyl(p-pentylbenzyl) ether,
6% 4-(5-octylpyrimidin-2-yl)phenyl(p-heptylbenzyl) ether,
18% 2-p-nonyloxyphenyl-5-nonylpyrimidine,
4% 2,3-dicyano-1,4-bis(trans-4-butoxycyclohexylcarboxy)benzene,
6% 2,3-dicyano-1,4-bis(trans-4-hexoxycyclohexylcarboxy)benzene and
3% 2,3-dicyano-1,4-bis(2-trans-4-pentylcyclohexylethyl)benzene has K/Sc 10°, Sc/N 66°, N/I 91.5° and $\Delta\epsilon$ of −1.0.

EXAMPLE 4

A liquid-crystalline phase consisting of
25% 4-(5-nonylpyrimidin-2-yl)phenyl(p-hexylbenzyl) ether,
30% 4-(5-nonylpyrimidin-2-yl)phenyl(p-propylbenzyl) ether,
10% 4-(5-hexylpyrimidin-2-yl)phenyl(p-octylbenzyl) ether,
10% 4-(5-octylpyrimidin-2-yl)phenyl(p-pentylbenzyl) ether,
10% 2-p-nonyloxyphenyl-5-nonylpyrimidine,
5% 2-p-hexyloxyphenyl-5-nonylpyrimidine,
8% 2,3-dicyano-1,4-bis(2-trans-4-hexylcyclohexylethyl)benzene and
2% 2,3-dicyano-1-(2-trans-4-butylcyclohexylethyl)-4-(trans-4-pentylcyclohexylmethoxy)benzene has K/Sc 11°, Sc/N 70°, N/I 98° and $\Delta\epsilon$ of −0.5.

EXAMPLE 5

A liquid-crystalline phase consisting of
18% 4-(5-nonylpyrimidin-2-yl)phenyl(p-heptylbenzyl) ether,
10% 4-(5-nonylpyrimidin-2-yl)phenyl(p-propylbenzyl) ether,
30% 4-(5-heptylpyrimidin-2-yl)phenyl(p-pentylbenzyl) ether,
22% 4-(5-hexylpyrimidin-2-yl)phenyl(p-pentylbenzyl) ether,
10% 2-p-nonyloxyphenyl-5-nonylpyrimidine,
8% 2,3-dicyano-1-(trans-4-pentylcyclohexylcarboxy)-4-(2-trans-4-pentylcyclohexylethyl)benzene and
2% 2,3-dicyano-1-(trans-4-heptylcyclohexylcarboxy)-4-(2-trans-4-heptylcyclohexylethyl)benzene has K/Sc 6°, Sc/N 90°, N/I 97° and $\Delta\epsilon$ of −1.0.

EXAMPLE 6

A liquid-crystalline phase consisting of
12% 4-(5-nonylpyrimidin-2-yl)phenyl(p-heptylbenzyl) ether,
12% 4-(5-nonylpyrimidin-2-yl)phenyl(p-propylbenzyl) ether,
9% 4-(5-nonylpyrimidin-2-yl)phenyl(p-pentylbenzyl) ether,
18% 4-(5-heptylpyrimidin-2-yl)phenyl(p-pentylbenzyl) ether,
11% 2-p-nonyloxyphenyl-5-nonylpyrimidine,
8% p-nonyloxyphenyl trans-4-octylcyclohexanecarboxylate,
8% p-hexyloxyphenyl trans-4-heptylcyclohexanecarboxylate,
10% p-heptylphenyl p-octyloxybenzoate,
4% 4'-hexylbiphenyl-4-yl p-pentylbenzoate,
4% 2-cyano-1,4-bis(trans-4-pentylcyclohexylcarboxy)benzene and
4% 2-cyano-1,4-bis(trans-4-heptylcyclohexylcarboxy)benzene has K/Sc 0°, Sc/N 66.5°, N/I 79° and $\Delta\epsilon$ of −2.3.

EXAMPLE 7

A liquid-crystalline phase consisting of
18% 4-(5-nonylpyrimidin-2-yl)phenyl(p-heptylbenzyl) ether,
23% 4-(5-nonylpyrimidin-2-yl)phenyl(p-pentylbenzyl) ether,
15% 4-(5-heptylpyrimidin-2-yl)phenyl(p-heptylbenzyl) ether,
14% 4-(5-heptylpyrimidin-2-yl)phenyl(p-pentylbenzyl) ether,
10% 2-p-nonyloxyphenyl-5-nonylpyrimidine,
5% p-heptylphenyl p-octyloxybenzoate,
10% 2,3-dicyano-1-(trans-4-butylcyclohexyl)-4-trans-4-hexylcyclohexyl)benzene and
5% 4'-hexylbiphenyl-4-yl p-pentylbenzoate, has K/Sc 6°, Sc/N 68.5°, N/I 81° and $\Delta\epsilon$ of −1.3.

EXAMPLE 8

A liquid-crystalline phase consisting of
17% 4-(5-heptylpyrimidin-2-yl)phenyl(p-pentylbenzyl) ether,
26% 4-(5-heptylpyrimidin-2-yl)phenyl(p-hexylbenzyl) ether,
13% 4-(5-nonylpyrimidin-2-yl)phenyl(p-pentylbenzyl) ether, 4% 4-(5-nonylpyrimidin-2-yl)phenyl(p-hexylbenzyl) ether,
30% r-1-cyano-1-octyl-cis-4-(4'-hexylbiphenyl-4-yl)cyclohexane,
5% r-1-cyano-1-pentyl-cis-4-(4'-pentylbiphenyl-4-yl)cyclohexane and
5% r-1-cyano-1-heptyl-cis-4-(4'-pentylbiphenyl-4-yl)cyclohexane has K/Sc 13°, Sc/N 70°, N/I 88.5° and $\Delta\epsilon$ of $-2.6$.

EXAMPLE 9

A liquid-crystalline phase consisting of
19% r-1-cyano-1-pentyl-cis-4-(4'-butylbiphenyl-4-yl)cyclohexane,
28% r-1-cyano-1-heptyl-cis-4-(4'-hexylbiphenyl-4-yl)cyclohexane,
15% r-1-cyano-butyl-cis-4-(4'-octylbiphenyl-4-yl)cyclohexane,
10% 4'-hexylbiphenyl-4-yl p-pentylbenzoate,
8% p-nonyloxyphenyl trans-4-octylcyclohexanecarboxylate,
14% p-hexyloxyphenyl trans-4-heptylcyclohexanecarboxylate and
6% p-octyloxyphenyl trans-4-heptylcyclohexanecarboxylate has K/Sc 13°, Sc/N 74°, N/I 90° and $\Delta\epsilon$ of $-4.7$.

EXAMPLE 10

A liquid-crystalline phase consisting of
23% r-1-cyano-1-pentyl-cis-4-(4'-pentylbiphenyl-4-yl)cyclohexane,
20% r-1-cyano-1-heptyl-cis-4-(4'-hexylbiphenyl-4-yl)cyclohexane,
18% r-1-cyano-1-butyl-cis-4-(4'-octylbiphenyl-4-yl)cyclohexane,
13% r-1-cyano-1-pentyl-cis-4-(4'-butylbiphenyl-4-yl)cyclohexane,
10% p-nonyloxyphenyl trans-4-octylcyclohexanecarboxylate,
10% p-hexyloxyphenyl trans-4-heptylcyclohexanecarboxylate,
3% 2,3-dicyano-1,4-bis(trans-4-pentylcyclohexylcarboxy)benzene and
3% 2,3-dicyano-1,4-bis(trans-4-propylcyclohexylcarboxy)benzene has K/Sc 15°, Sc/N 71°, N/I 94.5° and $\Delta\epsilon$ of $-5.3$.

EXAMPLE 11

A liquid-crystalline phase is prepared which consists of
4% 2-p-heptyloxyphenyl-5-heptylpyrimidine,
30% 2-p-undecyloxyphenyl-5-hexylpyrimidine,
30% 2-p-nonyloxyphenyl-5-nonylpyrimidine,
12% pentyl r-1-cyano-cis-4-[p-(5-heptylpyrimidin-2-yl)phenyl]cyclohexane-1-carboxylate,
14% butyl r-1-cyano-cis-4-[p-(5-octylpyrimidin-2-yl)phenyl]cyclohexane-1-carboxylate and
10% p-(5-hexylpyrimidin-2-yl)phenyl 2-chloropropionate (optically active).

EXAMPLE 12

A liquid-crystalline phase is prepared which consists of
20% 4-(5-hexylpyrimidin-2-yl)phenyl(p-pentylbenzyl) ether,
20% 4-(5-heptylpyrimidin-2-yl)phenyl(p-hexylbenzyl) ether,
20% 4-(5-nonylpyrimidin-2-yl)phenyl(p-propylbenzyl) ether,
5% 4-(5-nonylpyrimidin-2-yl)phenyl(p-cyanobenzyl) ether,
10% butyl r-1-cyano-cis-4-[p-(5-heptylpyrimidin-2-yl)phenyl]cyclohexane-1-carboxylate,
15% pentyl r-1-cyano-cis-4-[p-(5-octyl-pyrimidin-2-yl)phenyl]cyclohexane-1-carboxylate and
10% p-(5-hexylpyrimidin-2-yl)phenyl 2-chloropropionate (optically active).

EXAMPLE 13

A liquid-crystalline phase consisting of
95% r-1-cyano-1-butoxy-cis-4-(4'-octylbiphenyl-4-yl)cyclohexane and
5% r-1-cyano-1-(1-hydroxy-3-methylcyclohexyl)-trans-4-pentylcyclohexyl)cyclohexane (optically active)

has I 140° Ch 102° $S_A$* 93° Sc* 44° K and a spontaneous polarization P of 2.5 nC/cm$^2$.

EXAMPLE 14

A liquid-crystalline phase consisting of
50% r-1-cyano-1-butoxy-cis-4-(4'-octylbiphenyl-4-yl)cyclohexane and
50% 4'-octyloxybiphenyl-4-yl p-2-methylheptoxybenzoate (optically active)

has I 140° Ch 112° Sc* 55° K and P=9.8 nC/cm$^2$.

EXAMPLE 15

A liquid-crystalline phase consisting of
42% r-1-cyano-1-butoxy-cis-4-(4'-octylbiphenyl-4-yl)cyclohexane,
43% r-1-cyano-1-pentyl-cis-4-(4'-octylbiphenyl-4-yl)cyclohexane,
10% r-1-cyano-1-pentyl-cis-4-(4'-butylbiphenyl-4-yl)cyclohexane and
5% p-(5-hexylpyrimidin-2-yl)phenyl 2-chloropropionate (optically active)

has I 125° Ch 92° $S_A$* 70° Sc*<RT K and P=3.8 nC/cm$^2$.

EXAMPLE 16

A liquid-crystalline phase consisting of
30% r-1-cyano-1-octyl-cis-4-(4'-pentylbiphenyl-4-yl)cyclohexane,
34% r-1-cyano-1-pentyl-cis-4-(4'-octylbiphenyl-4-yl)cyclohexane,
18% r-1-cyano-1-butoxy-cis-4-(4'-octylbiphenyl-4-yl)cyclohexane,
8% r-1-cyano-1-pentyl-cis-4-(4'-butylbiphenyl-4-yl)cyclohexane and
10% p-(5-hexylpyrimidin-2-yl)phenyl 2-chloropropionate (optically active)

has I 109° Ch 89° $S_A$* 53° Sc*<RT K and P=1.8 nC/cm$^2$.

EXAMPLE 17

A liquid-crystalline phase consisting of
13% 4-(5-heptylpyrimidin-2-yl)phenyl(p-pentylbenzyl) ether,
16% 4-(5-heptylpyrimidin-2-yl)phenyl(p-hexylbenzyl) ether,
5% 4-(5-nonylpyrimidin-2-yl)phenyl(p-pentylbenzyl) ether,
12% 2-p-nonyloxyphenyl-5-nonylpyrimidine,
4% r-1-cyano-1-pentyl-cis-4-(4'-butylbiphenyl-4-yl)cyclohexane, 15% r-1-cyano-1-octyl-cis-4-(4'-pentylbiphenyl-4-yl)cyclohexane,
16% r-1-cyano-1-pentyl-cis-4-(4'-octylbiphenyl-4-yl)cyclohexane,
9% r-1-cyano-1-butoxy-cis-4-(4'-octylbiphenyl-4-yl)cyclohexane and
10% p-(5-hexylpyrimidin-2-yl)phenyl 2-chloropropionate (optically active)
has I 99° Ch 83° Sc* 35° K and P=5.5 nC/cm².

EXAMPLE 18

A ferroelectric smectic material consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
7% 2-p-hexyloxyphenyl-5-nonylpyrimidine,
23% 2-p-nonyloxyphenyl-5-nonylpyrimidine,
28% r-1-cyano-cis-4-(4'-butyloxybiphenyl-4-yl)-1-octylcyclohexane,
14% r-1-cyano-cis-4-(4'-hexyl-biphenyl-4-yl)-1-heptylcyclohexane,
6% R-1-cyano-1-(trans-4-pentylcyclohexyl)-cis-4-(trans-4-pentylcyclohexyl)cyclohexane and
10% p-(5-hexylpyrimidin-2-yl)phenyl 2-chloropropionate (optically active)
has a clearing point of 92° and a dielectric anisotropy $\Delta\epsilon$ of $-2.6$.

EXAMPLE 19

A liquid-crystalline phase consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
30% r-1-cyano-cis-4-(4'-octyloxybiphenyl-4-yl)-1-octylcyclohexane,
15% r-1-cyano-cis-4-(4'-nonanoyloxybiphenyl-4-yl)-1-butylcyclohexane and
10% r-1-cyano-cis-4-[p-(5-nonylpyrimidin-2-yl)phenyl]-1-(2-methylbutyl)cyclohexane (optically active)
has K $-8°$ S$_C^x$ 65° S$_A^x$ and P=8 nC/cm² at 20°.

EXAMPLE 20

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
30% r-1-cyano-cis-4-(4'-nonanoyloxybiphenyl-4-yl)-1-octylcyclohexane,
10% r-1-cyano-cis-4-(p-octylphenyl)-1-octylcyclohexane,
5% r-1-cyano-cis-4-(p-octylphenyl)-1-(2-methylbutyl)cyclohexane (optically active) and
10% r-1-cyano-cis-4-[p-(p-heptylphenoxycarbonyl)phenyl]-1-(2-methylbutyl)cyclohexane (optically active).

EXAMPLE 21

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
30% r-1-cyano-cis-4-(4'-nonanoyloxybiphenyl-4-yl)-1-octylcyclohexane,
10% r-1-cyano-cis-4-(p-octyloxyphenyl)-1-octylcyclohexane,
5% r-1-cyano-cis-4-(p-octyloxyphenyl)-1-(2-methylbutyl)cyclohexane (optically active) and
10% r-1-cyano-cis-4-[p-(p-heptylphenoxycarbonyl)phenyl]-1-(2-methylbutyl)cyclohexane (optically active).

EXAMPLE 22

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
30% r-1-cyano-cis-4-(4'-nonanoyloxybiphenyl-4-yl)-1-octylcyclohexane,
10% r-1-cyano-cis-4-(p-octanoyloxyphenyl)-1-octylcyclohexane,
.5% r-1-cyano-cis-4-(p-octanoyloxyphenyl)-1-(2-methylbutyl)cyclohexane (optically active) and
10% r-1-cyano-cis-4-[p-(p-heptylphenoxycarbonyl)phenyl]-1-(2-methylbutyl)cyclohexane (optically active).

EXAMPLE 23

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
30% r-1-cyano-cis-4-(4'-nonanoyloxybiphenyl-4-yl)-1-octylcyclohexane,
10% r-1-cyano-cis-4-(p-(2-methylbutoxy)phenyl)-1-octylcyclohexane,
5% r-1-cyano-cis-4-(p-(2-methylbutoxy)phenyl)-1-(2-methylbutyl)cyclohexane (optically active) and
10% r-1-cyano-cis-4-[p-(p-heptylphenoxycarbonyl)phenyl]-1-(2-methylbutyl)cyclohexane (optically active).

EXAMPLE 24

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
20% r-1-cyano-1-(trans-4-octylcyclohexylethyl)-cis-4-(p-octyloxyphenyl)cyclohexane,
10% r-1-cyano-1-(trans-4-octylcyclohexylethyl)-cis-4-(p-heptyloxyphenyl)cyclohexane,
10% r-1-cyano-1-(trans-4-octylcyclohexylethyl)-cis-4-(p-octylphenyl)cyclohexane, 5% r-1-cyano-1-(trans-4-octylcyclohexylethyl)-cis-4-(p-heptylphenyl)cyclohexane,
10% r-1-cyano-cis-4-[p-(5-octylpyrimidin-2-yl)phenyl]-1-(2-methylbutyl)cyclohexane (optically active).

EXAMPLE 25

A liquid-crystalline phase consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
30% r-1-cyano-cis-4-[p-(p-octyloxybenzoyloxy)phenyl]-1-octylcyclohexane,
15% r-1-cyano-cis-4-[p-(p-octyloxybenzoyloxy)phenyl]-1-pentylcyclohexane,
10% r-1-cyano-cis-4-[p-(5-nonyloxypyrimidin-2-yl)phenyl]-1-(2-methylbutyl)cyclohexane (optically active)
has K $-10°$ $S_C^x$ $61°$ $S_A^x$ and P=10 nC/cm$^2$ at 20°.

EXAMPLE 26

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
15% 1-cyano-1-trans-4-(p-heptyloxyphenyl)cyclohexyl-2-(trans-4-octylcyclohexyl)ethane,
15% 1-cyano-1-trans-4-(p-octyloxyphenyl)cyclohexyl)-2-(trans-4-octylcyclohexyl)ethane,
10% 1-cyano-1-trans-4-(p-octylphenyl)cyclohexyl-2-(trans-4-butylcyclohexyl)ethane,
5% 1-cyano-1-trans-4-(p-heptylphenyl)cyclohexyl-2-(trans-4-butylcyclohexyl)ethane and
10% r-1-cyano-cis-4-[p-(5-octylpyrimidin-2-yl)phenyl]-1-(2-methylbutyl)cyclohexane.

EXAMPLE 27

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
25% r-1-cyano-cis-4-(4'-heptyloxy-3'-fluorobiphenyl-4-yl)-1-nonylcyclohexane,
10% r-1-cyano-cis-4-(4'-octyloxy-3'-fluorobiphenyl-4-yl)-1-butylcyclohexane,
5% r-1-cyano-cis-4-[trans-4-(p-octylphenyl)cyclohexyl]-1-(2-methylbutyl)cyclohexane (optically active),
5% r-1-cyano-cis-4-[trans-4-(p-octyloxyphenyl)cyclohexyl]-1-(2-methylbutyl)cyclohexane (optically active) and
10% r-1-cyano-cis-4-[p-(p-octyloxyphenoxycarbonyl)phenyl]-1-heptylcyclohexane.

EXAMPLE 28

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
20% trans-4-(4'-octylbiphenyl-4-yl)-1-(1-cyanoheptyl)-cyclohexane,
10% trans-4-(4'-octylbiphenyl-4-yl)-1-(2-cyanobutyl)-cyclohexane,
10% trans-4-(4'-heptylbiphenyl-4-yl)-1-(1-cyanopentyl)cyclohexane,
5% trans-4-(4'-octylbiphenyl-4-yl)-1-(1-cyanobutyl)cyclohexane,
5% r-1-cyano-cis-4-[p-(p-octyloxyphenyl)benzoyloxy]-1-(2-methylbutyl)cyclohexane (optically active) and
5% r-1-cyano-cis-4-[p-(p-heptylphenyl)benzoyloxy]-1-(2-methylbutyl)cyclohexane.

EXAMPLE 29

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
10% r-1-cyano-cis-4-(p-octyloxyphenyl)-1-octylcyclohexane,
10% r-1-cyano-cis-4-(4'-octyloxycarbonylbiphenyl-4-yl)-1-octylcyclohexane,
5% r-1-cyano-cis-4-(p-heptyloxybenzoyloxy)-1-nonylcyclohexane,
10% r-1-cyano-cis-4-[p-(p-octylphenyl)benzoyloxy]-1-butylcyclohexane,
5% r-1-cyano-cis-4-[p-(p-octyloxyphenyl)benzoyloxy]-1-butylcyclohexane and
15% r-1-cyano-cis-4-[p-(p-nonylphenyl)benzoyloxy]-1-(2-methylbutyl)cyclohexane (optically active).

EXAMPLE 30

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
10% r-1-cyano-cis-4-(p-octyloxycarbonyloxyphenyl)-1-octylcyclohexane,
10% r-1-cyano-cis-4-(4'-octyloxycarbonylbiphenyl-4-yl)-1-octylcyclohexane,
5% r-1-cyano-cis-4-(p-heptyloxybenzoyloxy)-1-nonylcyclohexane,
10% r-1-cyano-cis-4-[p-(p-octylphenyl)benzoyloxy]-1-butylcyclohexane,
5% r-1-cyano-cis-4-[p-(p-octyloxyphenyl)benzoyloxy]-1-butylcyclohexane and
15% r-1-cyano-cis-4-[p-(p-nonylphenyl)benzoyloxy]-1-(2-methylbutyl)cyclohexane (optically active).

EXAMPLE 31

A liquid-crystalline phase is prepared consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine, 25% 2-p-nonyloxyphenyl-5-nonylpyrimidine,
10% r-1-cyano-cis-4-(p-octyloxyphenyl)-1-octylcyclohexane,
10% r-1-cyano-cis-4-(4'-octyloxycarbonylbiphenyl-4-yl)-1-octylcyclohexane,
5% r-1-cyano-cis-4-(p-heptyloxybenzoyloxy)-1-nonylcyclohexane,
10% r-1-cyano-cis-4-[p-(p-octylphenyl)benzoyloxy]-1-butylcyclohexane,
5% r-1-cyano-cis-4-[p-(p-octyloxyphenyl)benzoyloxy]-1-butylcyclohexane and
15% r-1-cyano-cis-4-[p-(5-nonylpyrimidin-2-yl)phenoxycarbonyl]-1-(2-methylbutyl)cyclohexane (optically active).

EXAMPLE 32

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
8% 2-p-hexyloxyphenyl-5-nonylpyrimidine,
25% 2-p-nonyloxyphenyl-5-nonylpyrimidine,
20% r-1-cyano-cis-4-octyl-1-[trans-4-(p-octyloxyphenyl)cyclohexylethyl]cyclohexane,
10% r-1-cyano-cis-4-butyl-1-[trans-4-(p-octyloxyphenyl)cyclohexylethyl]cyclohexane,
10% r-1-cyano-cis-4-nonyl-1-[trans-4-(p-heptylphenyl)cyclohexylethyl]cyclohexane,
5% r-1-cyano-cis-4-(2-methylbutyl)-1-[trans-4-(p-octylphenyl)cyclohexylethyl]cyclohexane (optically active),
5% r-1-cyano-cis-4-(p-octylphenoxycarbonyl)-1-nonylcyclohexane and
5% r-1-cyano-cis-4-[trans-4-(p-octylphenyl)cyclohexyl]-1-(2-methylbutyl)cyclohexane (optically active).

EXAMPLE 33

A liquid-crystalline phase consisting of
2% 2-p-hexyloxyphenyl-5-heptylpyrimidine,
2% 2-p-heptyloxyphenyl-5-heptylpyrimidine,
2% 2-p-octyloxyphenyl-5-heptylpyrimidine,
2% 2-p-nonyloxyphenyl-5-heptylpyrimidine,
7% 2-p-hexyloxyphenyl-5-nonylpyrimidine,
23% 2-p-nonyloxyphenyl-5-nonylpyrimidine,
30% r-1-cyano-cis-4-(4'-octyloxybiphenyl-4-yl)-1-octylcyclohexane,
8% r-1-cyano-cis-4-(4'-butylbiphenyl-4-yl)-1-octylcyclohexane,
14% r-1-cyano-cis-4-(4'-heptyloxybiphenyl-4-yl)-1-(2-methylbutyl)cyclohexane (optically active) and
10% 1-cyano-3-methyl-1-(4'-pentylbiphenyl-4-ylethyl)cyclohexane
has K/S* −29°, S*$_C$/S*$_A$ 66°, S*$_A$/Ch 72°, Ch/I 89°, P$_S$=30.2 nC/cm$^2$ at 20°, pitch in the chlolesteric phase: −21 μm, tilt angle 28° at 20° and a switching time of 315 μs at 2 μm and 12 V.

EXAMPLE 34

56 g of dicyclohexylcarbodiimide (DCC) in 50 ml of CH$_2$CCl$_2$ is added to a mixture, cooled to 0° C. of 67 g of 4-hydroxy-4'-heptylbiphenyl, 55.75 g of 4-cyano-4-pentylcyclohexanecarboxylic acid (obtainable from 4-cyanocyclohexanecarboxylic acid by alkylation with pentyl bromide in the presence of 2 equivalents of lithium diisopropylamide (LDA)), 3 g of 4-N,N'-dimethylaminopyridine (DMAP) and 400 ml of CH$_2$CCl$_2$ while cooling with ice. The ice bath is then removed and the reaction mixture is stirred for 3 hours at room temperature. The N,N'-dicyclohexylurea which precipitates is removed by filtration and the CH$_2$Cl$_2$ phase is washed consecutively with H$_2$O, 1N HCl and NaHCO$_3$ solution and dried over MgSO$_4$. After distilling off the solvent, the residue is purified by crystallization and column chromatography. r-1-Cyano-1-pentyl-cis-4-[p-(p-heptylphenyl)phenoxycarbonyl]cyclohexane is obtained.

r-1-Cyano-1-pentyl-cis-4-(p-heptylphenoxycarbonyl)cyclohexane and also the homologous 1-alkyl-1-cyanocyclohexyl compounds, the homologous p-alkylphenyl, p-alkoxyphenyl, p-alkanoyloxyphenyl compounds are obtained in an analogous manner.

EXAMPLE 35

22.7 g of DCC in 25 ml of CH$_2$Cl$_2$ are added at 0° C. to 5° C. to a mixture of 30 g of p-octyloxyphenol, 22 g of p-(4-cyano-4-pentylcyclohexyl)benzoic acid (obtainable from 4-phenylcyclohexanecarboxylic acid by conversion into 4-phenylcyclohexanecarbonitrile and subsequent alkylation of the nitrile with pentyl bromide in the presence of LDA as a base and Friedel-Crafts acylation of the aromatic compound with acetyl chloride in the presence of 2 equivalents of AlCl$_3$ and haloform degradation), 1.5 g of DMAP and 200 ml of CH$_2$Cl$_2$. Stirring is then continued for 3 hours at room temperature, and working-up is carried out as already described. r-1-Cyano-1-pentyl-cis-4-[p-(p-octyloxyphenoxycarbonyl)phenyl]cyclohexane is obtained.

The homologous 1-cyano-1-alkyl compounds, and also the homologous p-alkyl, p-alkoxy, p-alkanoyloxy and also p-alkoxycarbonyloxyphenoxycarbonyl compounds are obtained in an analogous manner.

EXAMPLE 36

22.7 g of DCC in 25 ml of CH$_2$CCl$_2$ are added as described above to a mixture of 25 g of p-octyloxybenzoic acid, 27 g of p-(4-cyano-4-pentylcyclohexyl)phenol (obtainable from p-methoxyphenylcyclohexanecarboxylic acid by conversion into p-methoxyphenylcyclohexanecarbonitrile and subsequent alkylation of the carbonitrile with pentyl bromide in the presence of LDA and subsequent splitting of the ether with iodotrimethylsilane), 1.5 g of DMAP and 200 ml of CH$_2$CCl$_2$. Working up is as usual r-1-Cyano-1-pentyl-cis-4-[p-(p-octyloxybenzoyloxy)phenyl]cyclohexane is obtained.

The homologous 1-cyano-1-alkyl compounds, and also the homologous p-alkyl, p-alkoxy, p-alkanoyloxy, p-alkoxycarbonyl and also p-alkoxycarbonyloxybenzoyloxy compounds are obtained in an analogous manner.

EXAMPLE 37

22.7 g of DCC in 25 ml of CH$_2$Cl$_2$ are added as usual to a mixture of 25 g of p-octyloxybenzoic acid, 28.5 g of 2-cyano-2-octyl-6-hydroxy-1,2,3,4-tetrahydronaphthalene (obtainable by Friedel-Crafts reaction of p-methoxyphenylacetyl chloride with ethene in the presence of a Lewis acid and subsequent conversion of the ketone thus obtained into the nitrile as described by C. W. Reese et al., JCS. Chem. Comm. 280, 1977, alkylation of the nitrile with octyl bromide in the presence of LDA as base and splitting of the ether with iodotrimethylsilane), 1.5 g of DMAP and 200 ml of CH$_2$Cl$_2$, and working up is then carried out as usual. 2-Cyano-2-octyl-6-(p- octyloxybenzoyloxy)-1,2,3,4-tetrahydronaphthalene is obtained. The homologous 2-cyano-2-alkyl compounds, and the homologous p-alkoxy, p-alkyl or p-alkanoyloxybenzoyloxy compounds are obtained in an analogous manner.

EXAMPLE 38

6.1 ml of a 15% solution of butyllithium in hexane is added dropwise at −20° to a solution of 1.4 ml of diisopropylamine in 10 ml of THF. Cooling is then carried out to −60°, a solution of 3.74 g of 1-cyano-4-(4-n-octylbiphenyl-4′-yl)cyclohexane in 10 ml of THF is added dropwise and stirring is continued for a further 15 minutes. 7.6 g of perfluorooctyl phenyliodoniumtrifluoromethanesulphonate is added in small amounts, stirring is carried out for a further 30 minutes at −60°, the cooling bath is removed and stirring is allowed to continue overnight at room temperature. 20 ml of 2N hydrochloric acid is added and extraction is carried out with dichloromethane. After working up the organic phase r-1-cyano-1-heptadecafluorooctyl-cis-4-(4-n-octylbiphenyl-4′-yl)cyclohexane is obtained.

EXAMPLE 39

2.9 g of r-1-cyano-1-hexyl-cis-4-(4-hydroxyphenyl)-cyclohexane and 0.8 g of pyridine are dissolved in 25 ml of toluene, 5.1 g of 4-perfluoroheptylbenzoyl chloride dissolved in 10 ml of toluene is added dropwise while stirring at 100° and the reaction is allowed to continue for 3 hours. After cooling the pyridine hydrochloride is filtered off with suction, the solvent evaporated and the residue purified by crystallization. r-1-Cyano-1-hexyl-cis-4-[4-(4-perfluoroheptylbenzoyloxy)phenyl]cyclohexane is obtained.

EXAMPLE 40

A mixture of 5.3 g of p-[p-(4-cyano-4-octylcyclohexyl)phenyl]phenol (obtainable by alkaline ether splitting from r-1-cyano-cis-4-(4′-propyloxybiphenyl-4-yl)-1-octylcyclohexane with potassium tert-butylate in NMP at 180°), 1.9 g of optically active 2-chloro-3-methylbutyric acid and 170 g of DMAP are suspended in 40 ml of CH$_2$Cl$_2$. 3.1 g of DCC in 5 ml of CH$_2$Cl$_2$ are then added dropwise at 0° and stirring is carried out for 12 hours at room temperature. After separating off the dicyclohexylurea and the usual working up, optically active 4′-(4-cyano-4-octylcyclohexyl)-biphenyl-4-yl 2-chloro-3-methylbutyrate is obtained, K 81 S$_A$ 138 I.

EXAMPLE 41

With air and moisture excluded, 9.4 ml of diisopropylamine, 4.6 g of butyronitrile and 30 g of trans-4-(4′-octylbiphenyl-4-yl)cyclohexylmethyl iodide [obtainable from trans-4-(4′octylbiphenyl-4-yl)cyclohexanecarboxylic acid (which can in turn be prepared by saponification of the nitrile) by reduction with LiAlH$_4$, conversion of the alcohol into the corresponding mesylate and subsequent Finkelstein reaction with NaI in acetone] are added in sequence to 50 ml of tetrahydrofuran at −50°. After heating to room temperature, stirring is carried out for a further hour and 4-octyl-4′-[trans-4-(2-cyanobutyl)cyclohexyl]biphenyl is obtained after the usual working up.

The following are obtained analogously by a reaction of the corresponding nitriles with the corresponding iodides:
4-butyloxy-4′-[trans-4-(1-cyanobutyl)cyclohexyl]biphenyl
4-pentyloxy-4′-[trans-4-(1-cyanobutyl)cyclohexyl]-biphenyl
4-hexyloxy-4′-[trans-4-(1-cyanobutyl)cyclohexyl]biphenyl
4-heptyloxy-4′-[trans-4-(1-cyanobutyl)cyclohexyl]-biphenyl
4-octyloxy-4′-[trans-4-(1-cyanobutyl)cyclohexyl]biphenyl, m.p. 74°, c.p. 165°
4-nonyloxy-4′-[trans-4-(1-cyanobutyl)cyclohexyl]-biphenyl
4-decyloxy-4′-[trans-4-(1-cyanobutyl)cyclohexyl]biphenyl
4-butyloxy-4′-[trans-4-(1-cyanooctyl)cyclohexyl]biphenyl
4-pentyloxy-4′-[trans-4-(1-cyanooctyl)cyclohexyl]-biphenyl
4-hexyloxy-4′-[trans-4-(1-cyanooctyl)cyclohexyl]biphenyl
4-heptyloxy-4′-[trans-4-(1-cyanooctyl)cyclohexyl]-biphenyl
4-octyloxy-4′-[trans-4-(1-cyanooctyl)cyclohexyl]biphenyl, m.p. 96°, c.p. 162°
4-nonyloxy-4′-[trans-4-(1-cyanooctyl)cyclohexyl]biphenyl
4-decyloxy-4′-[trans-4-(1-cyanooctyl)cyclohexyl]biphenyl

EXAMPLE 42

While cooling with ice, 4.54 g of dicyclohexylcarbodiimide in 10 ml of dichloromethane are added dropwise to a mixture of 6.24 g of 4-heptyloxy-4′-biphenylcarboxylic acid, 4.46 g of 4-cyano-4-heptylcyclohexanol [obtainable from trans-4-cyanocyclohexanol by protecting the hydroxyl group as THP ether, reaction with heptyl iodide and lithium diisopropylamide and subsequent cleavage of the protective group] and 0.2 g of 4-N,N′-dimethylaminopyridine in 45 ml of dichloromethane. After 25 hours, the precipitated urea derivative is filtered off by suction, the filtrate is diluted with methylene chloride and washing was carried out several times in sequence with dilute hydrochloric acid and with water. After drying, the removal of the solvent and purification by chromatography and crystallization, 4-cyano-4-heptylcyclohexyl 4-heptyloxy-4′-biphenylcarboxylate is obtained.

The following are prepared analogously:
4-cyano-4-heptylcyclohexyl 4-octyloxy-4′-biphenylcarboxylate
4-cyano-4-heptylcyclohexyl 4-nonyloxy-4′-biphenylcarboxylate
4-cyano-4-heptylcyclohexyl 4-decyloxy-4′-biphenylcarboxylate
4-cyano-4-heptylcyclohexyl 4-hexyloxy-4′-biphenylcarboxylate
4-cyano-4-heptylcyclohexyl 4-pentyloxy-4′-biphenylcarboxylate
4-cyano-4-heptylcyclohexyl 4-butyloxy-4′-biphenylcarboxylate
4-cyano-4-heptylcyclohexyl 4-heptyl-4′-biphenylcarboxylate
4-cyano-4-heptylcyclohexyl 4-octyl-4′-biphenylcarboxylate
4-cyano-4-heptylcyclohexyl 4-nonyl-4′-biphenylcarboxylate
4-cyano-4-heptylcyclohexyl 4-decyl-4′-biphenylcarboxylate
4-cyano-4-heptylcyclohexyl 4-butyloxy-2′-fluoro-4′-biphenylcarboxylate 4-cyano-4-heptylcyclohexyl 4-pentyloxy-2'-fluoro-4'-biphenylcarboxylate
4-cyano-4-heptylcyclohexyl 4-hexyloxy-2'-fluoro-4'-biphenylcarboxylate
4-cyano-4-heptylcyclohexyl 4-heptyloxy-2'-fluoro-4'-biphenylcarboxylate
4-cyano-4-heptylcyclohexyl 4-octyloxy-2'-fluoro-4'-biphenylcarboxylate
4-cyano-4-heptylcyclohexyl 4-nonyloxy-2'-fluoro-4'-biphenylcarboxylate
4-cyano-4-heptylcyclohexyl 4-decyloxy-2'-fluoro-4'-biphenylcarboxylate
4-cyano-4-heptylcyclohexyl 4-heptyl-2'-fluoro-4'-biphenylcarboxylate
4-cyano-4-heptylcyclohexyl 4-octyl-2'-fluoro-4'-biphenylcarboxylate
4-cyano-4-heptylcyclohexyl 4-nonyl-2'-fluoro-4'-biphenylcarboxylate
4-cyano-4-heptylcyclohexyl 4-decyl-2'-fluoro-4'-biphenylcarboxylate
4-cyano-4-heptylcyclohexyl 4-butyloxy-3'-fluoro-4'-biphenylcarboxylate
4-cyano-4-heptylcyclohexyl 4-pentyloxy-3'-fluoro-4'-biphenylcarboxylate
4-cyano-4-heptylcyclohexyl 4-hexyloxy-3'-fluoro-4'-biphenylcarboxylate
4-cyano-4-heptylcyclohexyl 4-heptyloxy-3'-fluoro-4'-biphenylcarboxylate
4-cyano-4-heptylcyclohexyl 4-octyloxy-3'-fluoro-4'-biphenylcarboxylate
4-cyano-4-heptylcyclohexyl 4-nonyloxy-3'-fluoro-4'-biphenylcarboxylate
4-cyano-4-heptylcyclohexyl 4-decyloxy-3'-fluoro-4'-biphenylcarboxylate
4-cyano-4-heptylcyclohexyl 4-heptyl-3'-fluoro-4'-biphenylcarboxylate
4-cyano-4-heptylcyclohexyl 4-octyl-3'-fluoro-4'-biphenylcarboxylate
4-cyano-4-heptylcyclohexyl 4-nonyl-3'-fluoro-4'-biphenylcarboxylate
4-cyano-4-heptylcyclohexyl 4-decyloxy-3'-fluoro-4'-biphenylcarboxylate
4-cyano-4-heptylcyclohexyl 4-butyloxy-3-fluoro-4'-biphenylcarboxylate
4-cyano-4-heptylcyclohexyl 4-pentyloxy-3-fluoro-4'-biphenylcarboxylate
4-cyano-4-heptylcyclohexyl 4-hexyloxy-3-fluoro-4'-biphenylcarboxylate
4-cyano-4-heptylcyclohexyl 4-heptyloxy-3-fluoro-4'-biphenylcarboxylate
4-cyano-4-heptylcyclohexyl 4-octyloxy-3-fluoro-4'-biphenylcarboxylate
4-cyano-4-heptylcyclohexyl 4-nonyloxy-3-fluoro-4'-biphenylcarboxylate
4-cyano-4-heptylcyclohexyl 4-decyloxy-3-fluoro-4'-biphenylcarboxylate
4-cyano-4-heptylcyclohexyl 4-heptyl-3-fluoro-4'-biphenylcarboxylate
4-cyano-4-heptylcyclohexyl 4-octyl-3-fluoro-4'-biphenylcarboxylate
4-cyano-4-heptylcyclohexyl 4-nonyl-3-fluoro-4'-biphenylcarboxylate
4-cyano-4-heptylcyclohexyl 4-decyloxy-3-fluoro-4'-biphenylcarboxylate
4-cyano-4-heptylcyclohexyl 4-butyloxy-2-fluoro-4'-biphenylcarboxylate
4-cyano-4-heptylcyclohexyl 4-pentyloxy-2-fluoro-4'-biphenylcarboxylate
4-cyano-4-heptylcyclohexyl 4-hexyloxy-2-fluoro-4'-biphenylcarboxylate
4-cyano-4-heptylcyclohexyl 4-heptyloxy-2-fluoro-4'-biphenylcarboxylate
4-cyano-4-heptylcyclohexyl 4-octyloxy-2-fluoro-4'-biphenylcarboxylate
4-cyano-4-heptylcyclohexyl 4-nonyloxy-2-fluoro-4'-biphenylcarboxylate
4-cyano-heptylcyclohexyl 4-decyloxy-2-fluoro-4'-biphenylcarboxylate
4-cyano-heptylcyclohexyl 4-heptyl-2-fluoro-4'-biphenylcarboxylate
4-cyano-4-heptylcyclohexyl 4-octyl-2-fluoro-4'-biphenylcarboxylate
4-cyano-4-heptylcyclohexyl 4-nonyl-2-fluoro-4'-biphenylcarboxylate
4-cyano-4-heptylcyclohexyl 4-decyloxy-2-fluoro-4'-biphenylcarboxylate
4-cyano-4-heptylcyclohexyl p-(trans-4-propylcyclohexyl)benzoate
4-cyano-4-heptylcyclohexyl p-(trans-4-propylcyclohexyl)benzoate
4-cyano-4-heptylcyclohexyl p-(trans-4-butylcyclohexyl)benzoate
4-cyano-4-heptylcyclohexyl p-(trans-4-pentylcyclohexyl)benzoate
4-cyano-4-heptylcyclohexyl p-(trans-4-hexylcyclohexyl)benzoate
4-cyano-4-heptylcyclohexyl p-(trans-4-heptylcyclohexyl)benzoate
4-cyano-4-heptylcyclohexyl p-(trans-4-octylcyclohexyl)benzoate
4-cyano-4-heptylcyclohexyl p-(trans-4-nonylcyclohexyl)benzoate
4-cyano-4-heptylcyclohexyl p-(trans-4-decylcyclohexyl)benzoate
4-cyano-4-heptylcyclohexyl trans-4-(trans-4-propylcyclohexyl)cyclohexanecarboxylate
4-cyano-4-heptylcyclohexyl trans-4-(trans-4-butylcyclohexyl)cyclohexanecarboxylate
4-cyano-4-heptylcyclohexyl trans-4-(trans-4-pentylcyclohexyl)cyclohexanecarboxylate
4-cyano-4-heptylcyclohexyl trans-4-(trans-4-hexylcyclohexyl)cyclohexanecarboxylate
4-cyano-4-heptylcyclohexyl trans-4-(trans-4-heptylcyclohexyl)cyclohexanecarboxylate
4-cyano-4-heptylcyclohexyl trans-4-(trans-4-octylcyclohexyl)cyclohexanecarboxylate
4-cyano-4-heptylcyclohexyl trans-4-(trans-4-nonylcyclohexyl)cyclohexanecarboxylate
4-cyano-4-heptylcyclohexyl trans-4-(trans-4-decylcyclohexyl)cyclohexanecarboxylate
4-cyano-4-heptylcyclohexyl p-(5-propylpyrimidine-2-yl)benzoate
4-cyano-4-heptylcyclohexyl p-(5-butylpyrimidine-2-yl)benzoate
4-cyano-4-heptylcyclohexyl p-(5-pentylpyrimidine-2-yl)benzoate
4-cyano-4-heptylcyclohexyl p-(5-hexylpyrimidine-2-yl)benzoate
4-cyano-4-heptylcyclohexyl p-(5-heptylpyrimidine-2-yl)benzoate
4-cyano-4-heptylcyclohexyl p-(5-octylpyrimidine-2-yl)benzoate
4-cyano-4-heptylcyclohexyl p-(5-nonylpyrimidine-2-yl)benzoate
4-cyano-4-heptylcyclohexyl p-(5-decylpyrimidine-2-yl)benzoate

| | |
|---|---|
| 4-cyano-4-heptylcyclohexyl yl)benzoate | p-(5-propylpyridine-2- |
| 4-cyano-4-heptylcyclohexyl yl)benzoate | p-(5-butylpyridine-2- |
| 4-cyano-4-heptylcyclohexyl yl)benzoate | p-(5-pentylpyridine-2- |
| 4-cyano-4-heptylcyclohexyl yl)benzoate | p-(5-hexylpyridine-2- |
| 4-cyano-4-heptylcyclohexyl yl)benzoate | p-(5-heptylpyridine-2- |
| 4-cyano-4-heptylcyclohexyl yl)benzoate | p-(5-octylpyridine-2- |
| 4-cyano-4-heptylcyclohexyl yl)benzoate | p-(5-nonylpyridine-2- |
| 4-cyano-4-heptylcyclohexyl yl)benzoate | p-(5-decylpyridine-2- |

EXAMPLE 43

5.6 g of dicyclohexylcarbodiimide in 50 ml of dichloromethane are added dropwise at 0° to a mixture of 6.3 g of 4-heptyl-4-cyanocyclohexanecarboxylic acid [m.p. 88°, obtainable from 4-cyanocyclohexanecarboxylic acid by alkylation with heptyl bromide and lithium diisopropylamide] 7.0 g of 4-octyl-4'-hydroxybiphenyl and 100 mg of 4-N,N'-dimethylaminopyridine in 150 ml of dichloromethane.

While being heated to room temperature, the reaction mixture is stirred for two hours, the precipitated urea is filtered off by suction and the filtrate is worked up as usual. 4-Octylbiphenyl-4'-yl r-1-cyano-1-heptylcyclohexane-cis-4-carboxylate is obtained, K 71 $S_B$ 100 $S_C$ 118 $S_A$ 161 N 165 I.

The corresponding esters are obtained analogously by reaction with the following hydroxy compounds or homologous compounds:

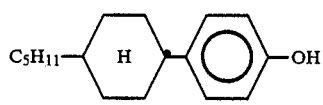

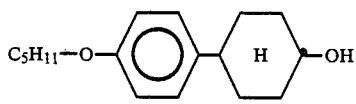

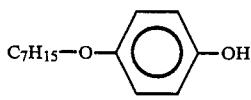

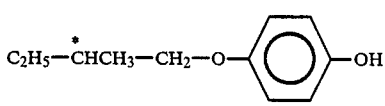

-continued

C$_5$H$_{11}$—[H]—[◯]—OH

C$_5$H$_{11}$—[◯]—[H]—OH

C$_5$H$_{11}$—O—[◯]—[H]—OH

C$_7$H$_{15}$—O—[◯]—OH

C$_2$H$_5$—CHCH$_3$—CH$_2$—O—[◯]—OH

EXAMPLE 44

Trans-4-pentylcyclohexyl (4-cyano-4-heptylcyclohexyl)methyl ether is obtained by reacting 4-cyano-4-heptylcyclohexylmethyl iodide [obtainable by reduction of ethyl 4-cyano-4-heptylcyclohexanecarboxylate with LiBH$_3$CN to the corresponding methyl alcohol, conversion into the mesylate and the reaction with NaI in acetone] with trans-4-pentyl-cyclohexanol in the presence of sodium hydride/diglyme.

The corresponding ethers from the cyclohexanols in Example 43 are obtained analogously.

EXAMPLE 45

A liquid-crystalline phase consisting of
2% 2-p-hexyloxyphenyl-5-heptylpyrimidine,
2% 2-p-heptyloxyphenyl-5-heptylpyrimidine,
2% 2-p-octyloxyphenyl-5-heptylpyrimidine,
2% 2-p-nonyloxyphenyl-5-heptylpyrimidine,
7% 2-p-hexyloxyphenyl-5-nonylpyrimidine,
25% 2-p-nonyloxyphenyl-5-nonylpyrimidine,
30% r-1-cyano-cis-4-(4'-octyloxybiphenyl-4-yl)-1-octyl-cyclohexane,
5% r-1-cyano-cis-4-(4'-hexylbiphenyl-4-yl)-1-heptylcyclohexane,
14% r-1-cyano-cis-4-(4'-heptyloxybiphenyl-4-yl)-1-(2-methylbutyl)cyclohexane (optically active) and
11% 1-cyano-3-methyl-2-(4'-pentylbiphenyl-4-ylethyl)cyclohexane (optically active) exhibits K/S*$_c$<−30°, S*$_c$/S$_A$ 65°, S$_A$/Ch 71°, Ch/I 87° P$_S$=32.7 nC/cm$^2$ at 20° and a switching time of 90 μs at 20° and 15 V/μm.

EXAMPLE 46

A liquid-crystalline phase consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
6% 2-p-hexyloxyphenyl-5-nonylpyrimidine,
25% 2-p-nonyloxyphenyl-5-nonylpyrimidine, 26% r-1-cyano-cis-4-(4'-butyloxybiphenyl-4-yl)-1-octylcyclohexane,
11% r-1-cyano-cis-4-(4'-hexylbiphenyl-4-yl)-1-heptylcyclohexane,
10% r-1-cyano-cis-4-(4'-octylbiphenyl-4-yl)-1-perfluorooctylcyclohexane and
10% ethyl 2-[p-(5-nonylpyrimidine-2-yl)phenoxy]propionate (optically active) exhibits $S_C^*/S_A$ 59°, $S_A$/Ch 75°, Ch/I 88° and $P_S = 8$ nC/cm².

EXAMPLE 47

A liquid-crystalline phase consisting of
3% 2-p-hexyloxyphenyl-5-octylpyrimidine,
3% 2-p-heptyloxyphenyl-5-octylpyrimidine,
3% 2-p-octyloxyphenyl-5-octylpyrimidine,
5% 2-p-hexyloxyphenyl-5-nonylpyrimidine,
5% 2-p-heptyloxyphenyl-5-nonylpyrimidine,
27% 2-p-nonyloxyphenyl-5-nonylpyrimidine,
25% r-1-cyano-cis-4-(4'-octyloxybiphenyl-4-yl)-1-octylcyclohexane,
10% r-1-cyano-cis-4-(4'-hexylbiphenyl-4-yl)-1-heptylcyclohexane,
10% p-(4-cyano-4-hexylcyclohexyl)phenyl p-perfluoroheptylbenzoate and
9% p-(5-hexylpyrimidine-2-yl)phenyl 2-chloropropionate (optically active) exhibits $S^*_C/S_A$ 64°, $S_A$/Ch 74°, Ch/I 87° and $P_S = 11$ nC/cm².

EXAMPLE 48

A liquid-crystalline phase consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
6% 2-p-hexyloxyphenyl-5-nonylpyrimidine,
10% 2-p-octyloxyphenyl-5-nonylpyrimidine,
14% 2-p-nonyloxyphenyl-5-nonylpyrimidine,
15% r-1-cyano-cis-4-(4'-octyloxybiphenyl-4-yl)-1-octylcyclohexane,
10% r-1-cyano-cis-4-(4'-butyloxybiphenyl-4-yl)-1-octylcyclohexane,
10% 4-octyloxy-4'-[trans-4-(1-cyanooctyl)cyclohexyl]biphenyl,
10% 1-cyano-3-methyl-1-(4'-pentylbiphenyl-4-ylethyl)cyclohexane (optically active) and
13% r-1-cyano-cis-4-(4'-heptyloxybiphenyl-4-yl)-1-(2-methylbutyl)cyclohexane (optically active) exhibits $S^*_C/S_A$ 61°, $S_A$/Ch 65°, Ch/I 84° and $P_S = 26$ nC/cm².

EXAMPLE 49

A ferroelectric smectic material is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
7% 2-p-hexyloxyphenyl-5-nonylpyrimidine,
23% 2-p-nonyloxyphenyl-5-nonylpyrimidine,
28% r-1-cyano-cis-4-(4'-butyloxybiphenyl-4-yl)-1-octylcyclohexane,
14% r-1-cyano-cis-4-(4'-hexylbiphenyl-4-yl)-1-heptylcyclohexane,
6% r-1-cyano-1-(trans-4-pentylcyclohexyl)-cis-4-(trans-4-pentylcyclohexyl)cyclohexane and
10% r-1-cyano-cis-4-[4'-(3,7-dimethyloctyloxy)biphenyl-4-yl]-1-octylcyclohexane (optically active).

EXAMPLE 50

A liquid-crystalline phase consisting of
3% 2-p-hexyloxyphenyl-5-octylpyrimidine,
3% 2-heptyloxyphenyl-5-octylpyrimidine,
3% 2-p-octyloxyphenyl-5-octylplyrimidine,
3% 2-p-nonyloxyphenyl-5-octylpyrimidine,
3% 2-p-hexyloxyphenyl-5-nonylpyrimidine,
3% 2-p-heptyloxyphenyl-5-nonylpyrimidine,
10% 2-p-octyloxyphenyl-5-nonylpyrimidine,
15% 2-p-nonyloxyphenyl-5-nonylpyrimidine,
15% r-1-cyano-cis-4-(4'-octyloxybiphenyl-4-yl)-1-octylcyclohexane,
18% r-1-cyano-cis-4-(4'-octyloxybiphenyl-4-yl)-1-nonylcyclohexane,
6% 4-octyloxy-4'-[trans-4-(1-cyanobutyl)cyclohexyl]biphenyl,
3% 4-octyl-4'-[trans-4-(2-cyanobutyl)cyclohexyl]biphenyl and
15% p-(5-octylpyrimidine-2-yl)phenyl 3-chloro-2-methylbutyrate (optically active) exhibits $S^*_C/S_A$ 68°, $S_A$/Ch 73°, Ch/I 88° and $P_S = 20$ nC/cm².

EXAMPLE 51

A liquid-crystalline phase consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
6% 2-p-hexyloxyphenyl-5-nonylpyrimidine,
23% 2-p-nonyloxyphenyl-5-nonylpyrimidine,
15% r-1-cyano-cis-4-(4'-octyloxybiphenyl-4-yl)-1-heptylcyclohexane,
15% r-1-cyano-cis-4-(4'-octyloxybiphenyl-4-yl)-1-octylcyclohexane,
5% 2-cyano-2-octyl-6-(p-heptyloxyphenyl)-trans-decalin,
5% (4'-hexylbiphenyl-4-yl) r-1-cyano-cis-4-pentylcyclohexancarboxylate,
10% 1-cyano-3-methyl-1-(4'-pentylbiphenyl-4-ylethyl)cyclohexane (optically active) and
9% r-1-cyano-cis-4-(4'-heptyloxybiphenyl-4-yl)-1-(2-methylbutyl)cyclohexane (optically active) exhibits $S^*_C/S_A$ 58°, $S_A$/Ch 65°, Ch/I 82° and $P_S = 24$ nC/cm².

EXAMPLE 52

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
6% 2-p-hexyloxyphenyl-5-nonylpyrimidine,
25% 2-p-nonyloxyphenyl-5-nonylpyrimidine,
3% r-1-cyano-cis-4-[4'-(trans-4-pentylcyclohexyl)biphenyl-4-yl]-1-pentylcyclohexane,
15% r-1-cyano-cis-4-(4'-octyloxybiphenyl-4-yl)-1-octylcyclohexane,
15% r-1-cyano-cis-4-(4'-octyloxybiphenyl-4-yl)-1-nonylcyclohexane,
16% r-1-cyano-cis-4-(4'-heptyloxybiphenyl-4-yl)-1-(2-methylbutyl)cyanohexane (optically active) and
8% r-1-cyano-cis-4-[4'-(7-cyanooctyloxy)biphenyl-4-yl]-1-hexylcyclohexane (optically active).

EXAMPLE 53

A liquid-crystalline phase is prepared consisting of
3% 2-p-hexyloxyphenyl-5-heptylpyrimidine, 3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
3% 2-p-hexyloxyphenyl-5-nonylpyridine,
3% 2-p-octyloxyphenyl-5-nonylpyridine,
23% 2-p-nonyloxyphenyl-5-nonylpyrimidine,
15% r-1-cyano-cis-4-(4'-octyloxybiphenyl-4-yl)-1-octylcyclohexane,
15% r-1-cyano-cis-4-(4'-octyloxybiphenyl-4-yl)-1-nonylcyclohexane,
15% r-1-cyano-cis-4-(4'-hexylbiphenyl-4-yl)-1-heptylcyclohexane,
4% r-1-cyano-cis-4-(4'-heptylmercaptobiphenyl-4-yl)-1-octylcyclohexane and
10% 1-cyano-3-methyl-1-(4'-pentylbiphenyl-4-yl-ethyl)cyclohexane (optically active).

EXAMPLE 54

A liquid-crystalline phase is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
6% 2-p-hexyloxyphenyl-5-nonylpyridine,
25% 2-p-nonyloxyphenyl-5-nonylpyrimidine,
15% r-1-cyano-cis-4-(4'-octyloxybiphenyl-4-yl)-1-octylcyclohexane,
15% r-1-cyano-cis-4-(4'-octyloxybiphenyl-4-yl)-1-nonylcyclohexane,
5% p-heptylphenyl p-(4-cyano-4-heptylcyclohexyl)-benzoate
5% p-(trans-4-propylcyclohexyl)-phenyl 1-cyano-4-pentylcyclohexanecarboxylate,
5% r-1-cyano-cis-4-(4'-hexylbiphenyl-4-yl)-1-heptylcyclohexane and
12% p-(5-nonylpyrimidine-2-yl)phenyl 2-chloro-3-methylbutyrate (optically active).

EXAMPLE 55

A liquid-crystalline phase consisting of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
6% 2-p-hexyloxyphenyl-5-nonylpyridine,
25% 2-p-nonyloxyphenyl-5-nonylpyrimidine,
15% r-1-cyano-cis-4-(4'-butyloxybiphenyl-4-yl)-1-octylcyclohexane,
15% r-1-cyano-cis-4-(4'-octyloxybiphenyl-4-yl)-1-octylcyclohexane,
3% r-1-cyano-cis-4-(4'-heptyloxybiphenyl-4-yl)-1-[2-(trans-4-pentylcyclohexyl)ethyl]cyclohexane,
5% r-1-cyano-cis-4-[p-(5-heptyldioxan-2-yl)phenyl]-1-hexylcyclohexane,
5% r-1-cyano-cis-4-(4'-butylbiphenyl-4-yl)-1-octylcyclohexane and
14% p-(5-hexylpyrimidine-2-yl)phenyl 2-chloro-3-methylbutyrate (optically active) exhibits $S^*_C/S_A$ 60°, $S_A/Ch$ 63°, Ch/I 83° and $P_S = 17$ nC/cm$^2$.

EXAMPLE 56

A ferroelectric smectic material is prepared which consists of
3% 2-p-hexyloxyphenyl-5-heptylpyrimidine,
3% 2-p-heptyloxyphenyl-5-heptylpyrimidine,
3% 2-p-octyloxyphenyl-5-heptylpyrimidine,
3% 2-p-nonyloxyphenyl-5-heptylpyrimidine,
7% 2-p-hexyloxyphenyl-5-nonylpyridine,
23% 2-p-nonyloxyphenyl-5-nonylpyrimidine,
28% r-1-cyano-cis-4-(4'-butyloxybiphenyl-4-yl)-1-octylcyclohexane,
14% r-1-cyano-cis-4-(4'-hexyl-biphenyl-4-yl)-1-heptylcyclohexane,
6% r-1-cyano-1-(trans-4-pentylcyclohexyl)-cis-4-(trans-4-pentylcyclohexyl)cyclohexane and
10% ethyl 2-[4'-(4-cyano-4-octylcyclohexyl)biphenyl-4-yloxy]propionate (optically active).

EXAMPLE 57

9.6 g of diethyl azodicarboxylate dissolved in tetrahydrofuran is added to a mixture of 19.4 g of 4-(4'-hydroxybiphenyl-4-yl)-1-cyano-1-octylcyclohexane, 6.5 g of ethyl lactate and 13.1 g of triphenylphosphene in 300 ml of tetrahydrofuran, stirring is carried out for one hour at 50°, the mixture is allowed to stand overnight, the solvent is removed and the residue is taken up in 100 ml of hot toluene. After the toluene solution has been cooled to 0°, it is filtered and the product is isolated from the filtrate as usual by chromatography. Optically active ethyl 2-[4'-(4-cyano-4-octylcyclohexyl)biphenyl-4-yloxy]propionate is obtained.

Analogous compounds are obtained by corresponding reaction of alkyl lactates with phenols of the formulae

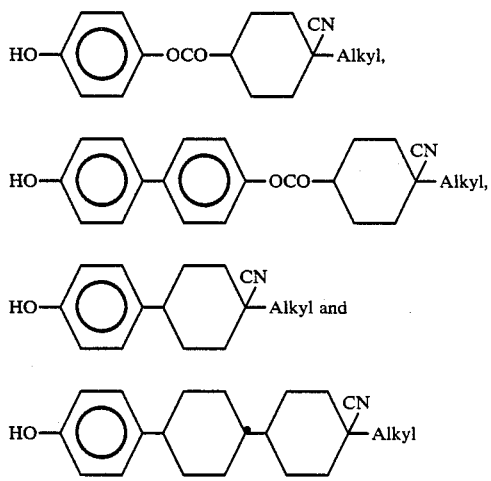

EXAMPLE 58

A solution of 11.5 g of diethylazodicarboxylate in tetrahydrofuran is added to a mixture of 20.6 g of 4-cyano-4-heptylcyclohexyl p-hydroxybenzoate (obtainable by esterification of 4-cyano-4-heptylcyclohexanol with p-benzyloxybenzoic acid and cleavage of the benzyl group by catalytic hydrogenation), 11.5 g of optically active hexyl lactate and 15.7 g of triphenylphosphine in 150 ml of tetrahydrofuran, stirring is carried out for one hour at 50° and the solvent is removed after 12 hours. The residue is dissolved in 100 ml of hot toluene, cooled down, filtered and the filtrate purified as usual by chromatography and crystallization. Optically active hexyl p-(4-cyano-4-heptylcyclohexyloxycarbonyl)phenoxypropionate is obtained.

Analogous compounds are obtained by corresponding reaction of alkyl lactates with phenols of the formula

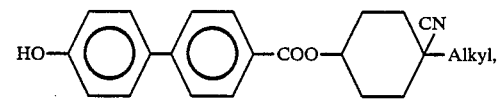

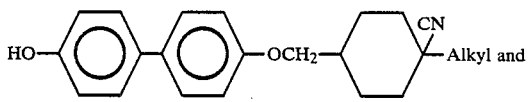

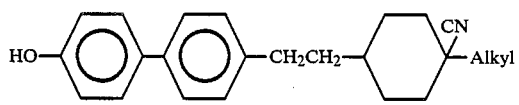

We claim:
1. In a liquid crystal phase having ferroelectric properties useful for rapidly switching displays and comprising at least two liquid crystalline compounds which form an achiral base mixture having a tilted smectic phase, and a chiral doping substance, the improvement wherein at least one compound of the achiral base mixture is of the formula

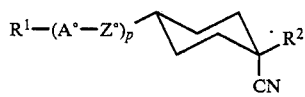

wherein
R¹ and R² are each independently of each other an alkyl group or a polyfluoroalkyl group containing 1 to 15 C atoms in each case, wherein one or more CH₂ groups or CF₂ groups may also be replaced by a group selected from the group consisting of —O—, —S—, —CO—, —CHhalogen—, —CH-CN—, —O—CO—, —O—COO—, —CO—O— and —CH=CH— or else by a combination of two suitable said groups, two hetero atoms not being directly linked to each other;
A° is unsubstituted 1,4-phenylene or 1,4-phenylene substituted singly or multiply by halogen atoms wherein one or more CH groups may also be replaced by N (Ph);
Z° denotes —CO—O—, —O—CO—, —CH₂O—, —OCH₂—, —CH₂CH₂— or a single bond; and
P denotes 2 or 3.
2. A liquid crystal phase according to claim 1, wherein R¹ is straight-chain alkoxy, alkanoyloxy, alkoxycarbonyl or alkoxycarbonyloxy each having 5 to 12 C atoms.
3. A liquid crystal phase according to claim 1, wherein R² is straight-chain alkyl of 5 to 12 C atoms.
4. A liquid crystal phase according to claim 1, wherein p is 2.
5. A liquid crystal phase according to claim 1, wherein (A°-Z°)ₚ is selected from the following formulae

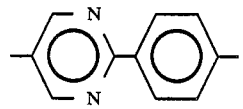

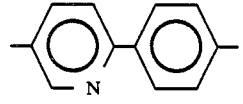

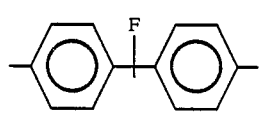

wherein the formula

represents 2- or 2'-fluoro biphenylene
6. In a ferroelectric electrooptical display element comprising a liquid crystal phase having ferroelectric properties, the improvement wherein said phase is one of claim 1.
7. A ferroelectric display element of claim 6 capable of operating by the SSFLC mechanism.
8. A liquid crystal phase according to claim 1, wherein (A°-Z°)ₚ is selected from the following formulae

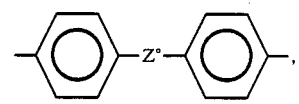

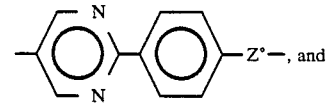

and Z° is not a direct bond.
9. In a liquid crystal phase having ferroelectric properties useful for rapidly switching displays and comprising at least two liquid crystalline compounds which form an achiral base mixture having a tilted smectic phase, and a chiral doping substance, the improvement wherein at least one compound of the achiral base mixture is of the formula

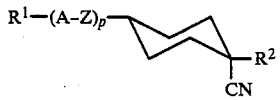

wherein
R¹ and R² are each independently of each other an alkyl group containing 1 to 15 C atoms in each case, wherein one or more CH₂ groups may also be replaced by a group selected from the grouping consisting of —O—, —S—, —CO—, —CH-halogen—, —CHCN—, —O—CO—, —O—COO—, —CO—O— and —CH=CH— or else by a combination of two suitable said groups, two hetero atoms not being directly linked to each other;

A is unsubstituted 1,4-phenylene or 1,4-phenylene substituted singly or multiply by halogen atoms wherein one or more CH groups may also be replaced by N (Ph);

Z denotes —CO—O—, —O—CO—, —CH₂O—, —OCH₂—, —CH₂CH₂—, or a single bond; and

P denotes 2 or 3.

* * * * *